US012807760B2

(12) United States Patent
Abdulhamid

(10) Patent No.: US 12,807,760 B2
(45) Date of Patent: Nov. 24, 2026

(54) TRÖGER'S BASE-DERIVED DIANHYDRIDE POLYIMIDE-BASED MEMBRANES FOR GAS SEPARATION

(71) Applicant: KING FAHD UNIVERSITY OF PETROLEUM AND MINERALS, Dhahran (SA)

(72) Inventor: Mahmoud Atef Abdulhamid, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 541 days.

(21) Appl. No.: 18/516,186

(22) Filed: Nov. 21, 2023

(65) Prior Publication Data

US 2025/0163219 A1 May 22, 2025

(51) Int. Cl.

*C08G 73/10* (2006.01)
*C07D 491/22* (2006.01)
*C08J 5/18* (2006.01)

(52) U.S. Cl.

CPC ....... *C08G 73/1085* (2013.01); *C07D 491/22* (2013.01); *C08G 73/1032* (2013.01); *C08J 5/18* (2013.01); *C08J 2379/08* (2013.01)

(58) Field of Classification Search

CPC .... C08G 73/1085; C08G 73/1032; C08J 5/18; C08J 2379/04
See application file for complete search history.

(56) References Cited

U.S. PATENT DOCUMENTS

| | | | |
|---|---|---|---|
| 2020/0165189 A1 | 5/2020 | Abdulhamid et al. | |
| 2020/0199141 A1* | 6/2020 | Ma | C07D 493/04 |

FOREIGN PATENT DOCUMENTS

| | | | |
|---|---|---|---|
| CN | 106749297 A | 5/2017 | |
| CN | 113666940 A | 11/2021 | |
| WO | 2017/212382 A1 | 12/2017 | |

OTHER PUBLICATIONS

I. Ma et al Facile Synthesis of a Hydroxyl-Functionalized Troger's Base Diamine: A New Building Block for High-Performance Polyimide Gas Separation Membranes, Macromolecules 2017, 50, 9569-9576, published Dec. 4, 2017.*

Ma et al. ; Design and Synthesis of Polyimides Based on Carbocyclic Pseudo-Tröger's Base-Derived Dianhydrides for Membrane Gas Separation Applications ; Macromolecules ; May 20, 2017 ; 8 Pages.

Veale et al. ; Synthesis, Photophysical, and DNA Binding Studies of Fluorescent Troger's Base Derived 4-Amino-1,8-naphthalimide Supramolecular Clefts ; J. Org. Chem. 2010, 75 ; Jul. 22, 2010 ; 13 Pages.

* cited by examiner

*Primary Examiner* — Gregory Listvoyb
(74) *Attorney, Agent, or Firm* — Oblon, McClelland, Maier & Neustadt, L.L.P.

(57) ABSTRACT

A Tröger's base (TB) complex including a chemical structure I where 'X' is O or N—$R_1$, $R_1$ is an aryl group, a substituted aryl group, a heteroaryl group, a Tröger's base compound, or a substituted Tröger's base compound. Further, a polyimide including the TB complex. The TB complex can be used in membrane films.

(I)

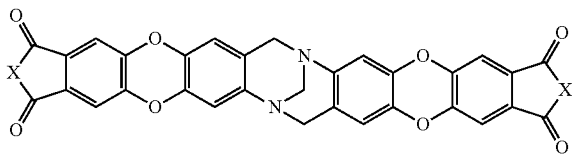

v (TBDA)

20 Claims, 14 Drawing Sheets i ii iii iv v (TBDA)

TBDA-TMPD

TBDA-HTB

TBDA-HTB

TRÖGER'S BASE-DERIVED DIANHYDRIDE POLYIMIDE-BASED MEMBRANES FOR GAS SEPARATION

STATEMENT OF ACKNOWLEDGEMENT

Support provided by the College of Petroleum Engineering and Geoscience, King Fahd University of Petroleum and Minerals, Saudi Arabia, through Project SF21012 is gratefully acknowledged.

STATEMENT REGARDING PRIOR DISCLOSURE BY THE INVENTOR

Aspects of the present disclosure are described in Abdulhamid, Mahmoud A., "Tröger's base-derived dianhydride as a promising contorted building block for polyimide-based membranes for gas separation" published in Volume 310, Separation and Purification Technology on Apr. 1, 2023, which is incorporated herein by reference in its entirety.

BACKGROUND

Technical Field

The present disclosure is directed towards a membrane-based separation application, particularly to a multi-layered Tröger's base-derived dianhydride complex used as a building block for polyimide-based membranes for gas separation.

Description of Related Art

The "background" description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present invention.

Membrane processes for gas separation are gaining a larger acceptance in industry and are competing with consolidation operations. Gas separation across a membrane is a pressure-driven process, where the driving force is the difference in pressure between the inlet of raw material and the outlet of the product. Traditionally, the membrane used in the process is a non-porous layer. The performance of the membrane depends on permeability and selectivity of a gas. Permeability is affected by the penetrant size, where larger gas molecules have a lower diffusion coefficient. The polymer chain flexibility and free volume in the polymer of the membrane material influences the diffusion coefficient, as the space within the permeable membrane must be large enough for the gas molecules to diffuse across. Permeability is the ability of the membrane to allow the permeating gas to diffuse through the material of the membrane as a consequence of the pressure difference over the membrane. The selectivity of a membrane is a measure of the ratio of permeability of the relevant gases for the membrane. Traditional membrane separation techniques, such as pressure swing absorption and cryogenic distillation, are inefficient in challenging and harsh environments. Polyimides have attracted attention as high-performance polymer materials for membrane-based separation applications due to their thermal stability, mechanical properties, solution-processability, and structural tunability.

Gas separation was shown in soluble polyimides prepared from a commonly used dianhydride, 4,4'-(hexafluoroisopropylidene)diphthalic anhydride (6FDA), and various diamines units. Although the obtained selectivity was good, the permeability could use improvement. During the last three decades, different strategies were developed to boost membrane performance by incorporating fillers, blends, thermal annealers, and developing new contorted building blocks. Amongst the different strategies, the synthesis of new contorted building blocks allows fine-tuning of the structure to achieve higher separation performance. Contorted building blocks contribute to higher gas separation performance, due to their potential to improve insufficient packing of polymer chains, potential to increase fractional free volume, and potential to enhance membrane permeability.

Polyimides are made from diamines and dianhydrides, splitting the development of building blocks into two parts: i) diamine and ii) dianhydride synthesis. Due to the lesser complexity of diamine preparation, various contorted diamines were developed and used for the preparation of polyimides for gas separation applications, such as Tröger's base-, Tröger's base carbocyclic pseudo counterpart-, triptycene-, ethanoanthracene-, and catalytic arene-norbornene annulation (CANAL)-based diamines. Tröger's base-based diamines were investigated due to their V-shaped structure, simple chemistry, and various starting materials availability, allowing a tailoring the diamines to improve specific separation features. For instance, methyl substituted Tröger's base-based diamine was reacted with 6FDA, pyromellitic dianhydride (PMDA), and bisanhydride of 3,3,3',3'-tetramethyl-6,6',7,7'-tetracarboxy-1,1'-spirobisindane (SBIDA) to achieve high gas permeability and moderate selectivity [M. Lee, C. G. Bezzu, M. Carta, P. Bernardo, G. Clarizia, J. C. Jansen, N. B. McKeown, Enhancing the Gas Permeability of Tröger's Base Derived Polyimides of Intrinsic Microporosity, *Macromolecules.* 49 (2016) 4147-4154]. Moreover, polyimides prepared from hydroxyl-functionalized Tröger's base diamine (HTB) exhibited a $CO_2/CH_4$ selectivity of 73 and a $CO_2$ permeability of 67 barrer [X. Ma, M. Abdulhamid, X. Miao, I. Pinnau, Facile Synthesis of a Hydroxyl-Functionalized Tröger's Base Diamine: A New Building Block for High-Performance Polyimide Gas Separation Membranes, *Macromolecules.* 50 (2017) 9569-9576]. This combination of selectivity and permeability allowed 6FDA-HTB to reach the 2008 $CO_2/CH_4$ selectivity upper bound, indicating the role of selecting a combination of diamines and dianhydride.

Although diamines have been investigated, the development of new dianhydrides was less progressed due to various challenges associated with dianhydride synthesis, such as solubility of dianhydrides, purity, and solubility of the polyimides. The contorted dianhydrides are limited to triptycene-, ethanoanthracene-, carbocyclic pseudo-Tröger's base-, spirobisindane-, and spirobifluorene-based dianhydride.

Therefore, further development of new contorted dianhydrides will provide a better understanding of diamine and dianhydride selection and also allow for improved separations by fine-tuning their chemical structure. Therefore, it is one object of the present disclosure to provide Tröger's base-based dianhydride (TBDA) and its corresponding polyimides as contorted building blocks for gas separation membranes to overcome the limitations of the art.

SUMMARY

In an exemplary embodiment, a Tröger's base (TB) complex is disclosed. The TB complex includes a chemical structure as described:

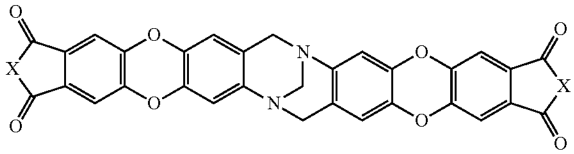

v (TBDA)

The X in the above complex is O or N—$R_1$. Further, $R_1$ is a comomoner selected from the group comprising of an aryl group, a heteroaryl group, a Tröger's base compound, or a substituted Tröger's base compound.

In another exemplary embodiment, a polyimide is disclosed. The polyimide includes reacted units of Tröger's base complex as described above. The X is N—$R_1$, and the comonomer $R_1$ is a substituted aryl group.

In some embodiments, the substituted aryl group is a 2,3,5,6-tetramethyl-p-phenylenediamine (TMPD).

In some embodiments, a membrane film is disclosed. The membrane film includes reacted units of Tröger's base complex as described above and 2,3,5,6-tetramethyl-p-phenylenediamine (TMPD).

In some embodiments, the polyimide includes reacted units of the Tröger's base complex as described above. Further, the X is N—$R_1$ and the comonomer $R_1$ is a substituted Tröger's base compound.

In some embodiments, the substituted Tröger's base compound is a 1,7-diamino-6H,12H-5,11-methanodibenzo[1,5] diazocine-2,8-diol (HTB).

In some embodiments, a film membrane is disclosed. The film membrane includes reacted units of Tröger's base complex as described above and HTB.

In some embodiments, a method of making the polyimide is disclosed. The method includes heating the TB complex of Formula I with a phenol to a first temperature to form a reaction mixture and the X is O. Further, the method includes adding the comonomer to the reaction mixture; and heating the reaction mixture to a second temperature. Furthermore, the method includes precipitating the reaction mixture in a first organic solvent to form a solid, precipitating the solid in a second organic solvent to form the polyimide, and drying the polyimide.

In some embodiments, the membrane film has a decomposition temperature of 410° C. to 440° C. by TGA.

In some embodiments, the gas permeability of the membrane film is in the following order: carbon dioxide>hydrogen>oxygen>methane>nitrogen.

In some embodiments, the gas permeability of the membrane film is in the following order: hydrogen>carbondioxide>oxygen>nitrogen>methane.

In some embodiments, the membrane film comprises hydrogen bonds.

In some embodiments, the membrane film has a $CO_2$ permeability of 1400 barrer to 1500 barrer.

In some embodiments, the membrane film has a $CO_2$ permeability of 60 barrer to 80 barrer.

In some embodiments, the membrane film has a $CO_2/CH_4$ selectivity of 15 to 25.

In some embodiments, the membrane film has a $CO_2/CH_4$ selectivity of 30 to 60.

In some embodiments, the membrane film has a diffusion coefficient of $CO_2$ of $2.0\times10^{-7}$ $cm^2$ $s^{-1}$ to $5.0\times10^{-7}$ $cm^2$ $s^{-1}$.

In some embodiments, the membrane film has a diffusion coefficient of $CO_2$ of $2.0\times10^{-1}$ $cm^2$ $s^{-1}$ to $3.0\times10^{-1}$ $cm^2$ $s^{-1}$.

In some embodiments, after aging for 80 days to 100 days, the membrane film has a higher $H_2/N_2$, $H_2/CH_4$, $O_2/N_2$, and $CO_2/CH_4$ selectivity compared to the membrane film before the aging.

In some embodiments, after aging for 40 days to 60 days, the membrane film has a higher $H_2/N_2$, $H_2/CH_4$, $O_2/N_2$, and $CO_2/CH_4$ selectivity compared to the membrane film before the aging.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
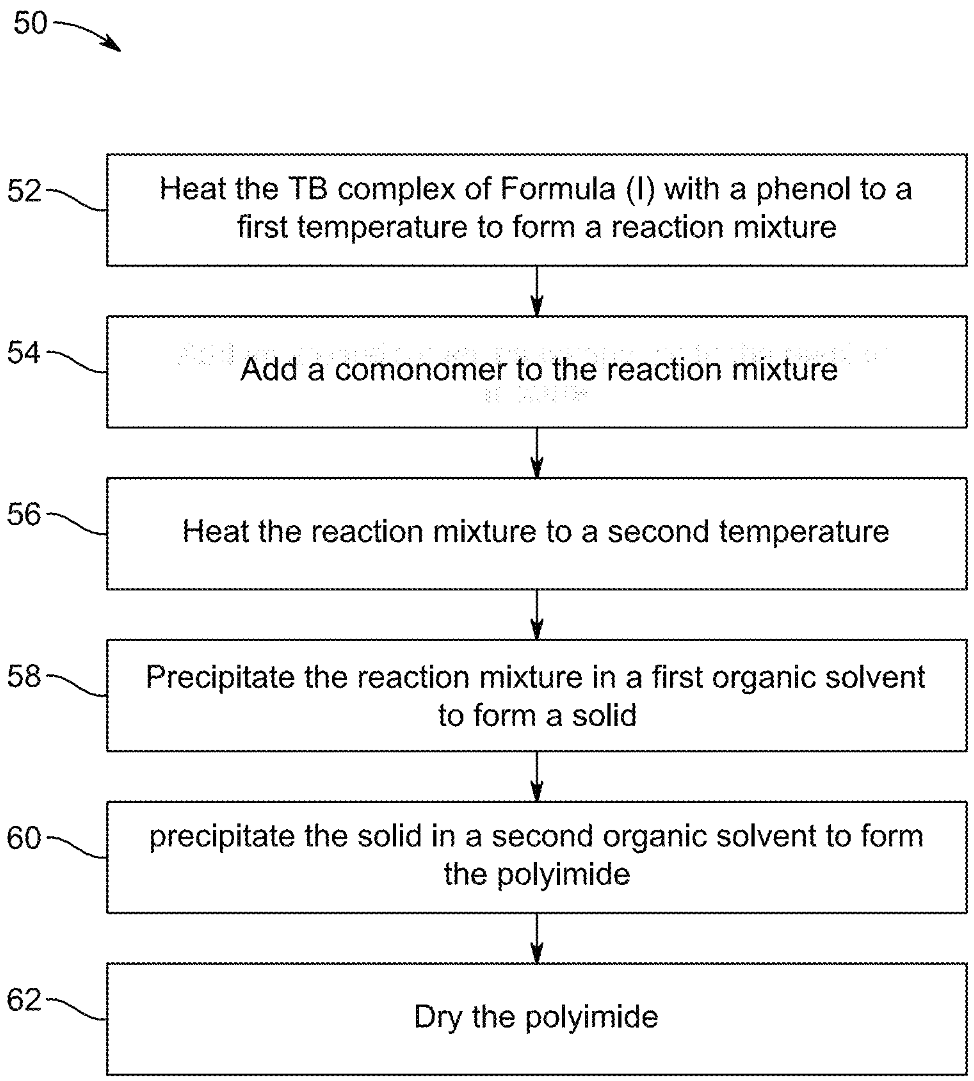
FIG. 1A is a flowchart depicting a method of preparing a polyamide membrane, according to certain embodiments.

In the following description, it is understood that other embodiments may be utilized, and structural and operational changes may be made without departure from the scope of the present embodiments disclosed herein.

When describing the present disclosure, the terms used are to be construed in accordance with the following definitions, unless a context dictates otherwise. Embodiments of the present disclosure will now be described more fully hereinafter with reference to the accompanying drawings wherever applicable in which some, but not all, embodiments of the disclosure are shown.

Reference will now be made to specific embodiments or features, examples of which are illustrated in the accompanying drawings. In the drawings, whenever possible, corresponding or similar reference numerals will be used to designate identical or corresponding parts throughout the several views. Moreover, references to various elements described herein are made collectively or individually when there may be more than one element of the same type; however, such references are merely exemplary in nature. It may be noted that any reference to elements in the singular may also be constructed to relate to the plural and vice-versa without limiting the scope of the disclosure to the exact number or type of such elements unless set forth explicitly in the appended claims. Further, as used herein, the words “a,” “an,” and the like generally carry a meaning of “one or more,” and “at least one,” unless stated otherwise.

Furthermore, the terms “approximately,” “approximate,” “about,” and similar terms generally refer to ranges that include the identified value within a margin of 20%, 10%, or preferably 5%, and any values therebetween.

The use of the terms “include,” “includes,” “including,” “have,” “has,” or “having” should be generally understood as open-ended and non-limiting unless specifically stated otherwise.

As used herein, “substituted” refers to all permissible substituents of the compounds described herein. Substituted refers to at least one hydrogen atom that is replaced with a non-hydrogen group, provided that normal valencies are maintained and that the substitution results in a stable compound. In the broadest sense, the permissible substituents include acyclic and cyclic, branched and unbranched, carbocyclic and heterocyclic, aromatic and nonaromatic substituents of organic compounds. Non-limiting examples of substituents include halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, arylalkyl, heteroaryl, substituted heteroaryl, halo (e.g., chloro, bromo, iodo, fluoro), hydroxyl, alkoxy, substituted alkoxy, alkoxycarbonyl, oxo, alkanoyl, aryloxy, alkanoyloxy, phenoxy, substituted phenoxy, aroxy, substituted aroxy, thiol, substituted thiol, alkylthio, substituted alkylthio, phenylthio, substituted phenylthio, arylthiol, substituted arylthio, arylalkylthio, alkylthiono, arylthiono, arylalkylthiono, cyano, isocyano, substituted isocyano, carbonyl, substituted carbonyl, carboxyl, substituted carboxyl, amino, substituted amino, alkylamino, cycloalkylamino, arylamino, arylalkylamino, disubstituted amino, alkanoylamino, aroylamino, arylalkanoylamino, amido, substituted amido, sulfonyl, substituted sulfonyl, alkyl sulfonyl, aryl sulfonyl, arylalkylsulfonyl, sulfonamide, substituted sulfonamide, sulfonic acid, nitro, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, polypeptide groups, and mixtures thereof. Non limiting examples of substituents (or functional groups, moieties, etc.) include —OH, —F, —Cl, —Br, —I, $—NH_2$, $—NO_2$, —COOH, $—CO_2CH_3$, —CN, —SH, $—CH_3$, $—OCH_3$, $—OCH_2CH_3$, $—C(O)CH_3$, $—N(CH_3)_2$, $—C(O)NH_2$, or $—OC(O)CH_3$. The substituents may themselves be optionally substituted and may be either unprotected, or protected as necessary, as known to those skilled in the art.

The term “alkyl”, as used herein, unless otherwise specified, refers to a straight, branched, or cyclic, saturated aliphatic fragment having 1 to 26 carbon atoms, (e.g., $C_1$, $C_2$, $C_3$, $C_4$, $C_5$, $C_6$, $C_7$, $C_8$, $C_9$, $C_{10}$, $C_{11}$, etc.) and specifically includes, but is not limited to, methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, tetradecyl, pentadecyl, hexadecyl, heptadecyl, octadecyl, nonadecyl, eicosyl, guerbet-type alkyl groups (e.g., 2-methylpentyl, 2-ethylhexyl, 2-propylheptyl, 2-butyloctyl, 2-pentylnonyl, 2-hexyldecyl, 2-heptylundecyl, 2-octyldodecyl, 2-nonyltridecyl, 2-decyltetradecyl, and 2-undecylpentadecyl), as well as cyclic alkyl groups (cycloalkyls) such as cyclopropyl, cyclobutyl, cyclopentyl, cyclohexyl, norbornyl, and adamantyl.

As used herein, “aryl” refers to a mono-, bi-, or tri-cyclic aromatic hydrocarbon moiety of 6 to 15 ring atoms, which is optionally substituted with one or more, typically one, two, or three, substituents within the ring structure or that replace a hydrogen. When two or more substituents are present in an aryl group, each substituent is independently selected. An aryl may refer to a carbocyclic aromatic monocyclic group containing 6 carbon atoms, which may be further fused to a second 5- or 6-membered carbocyclic group, which may be aromatic, saturated, or unsaturated. Exemplary aryl includes, but is not limited to, benzene, phenyl, anthracenyl, indanyl, 1-naphthyl, 2-naphthyl, tetrahydronaphthyl, and the like, each of which can optionally be substituted. The fused aryls may be connected to another group either at a suitable position on the cycloalkyl/cycloalkenyl ring or the aromatic ring.

The term “arylalkyl”, as used herein, refers to a straight or branched chain alkyl moiety (as defined above), that is substituted with an aryl group (as defined above), examples of which include, but are not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

As used herein, “heteroaryl group” refers to a monovalent mono- or bicyclic aromatic moiety of 5 to 12 ring atoms containing one, two, or three ring heteroatoms selected from N, O, or S, the remaining ring atoms being C. The heteroaryl ring can be optionally substituted with one or more substituents, typically one or two substituents. Exemplary heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzo thiophenyl, dibenzofuran, and benzodiazepin-2-one-5-yl, and the like.

As used herein, the term “alkoxy” refers to an alkyl group which is singularly bonded to oxygen; thus R—O, where R has $C_1$-$C_{10}$ carbon atoms.

As used herein, “Tröger's base” refers to any Tröger's base and/or any derivative thereof. Tröger's base is a white solid tetracyclic organic compound with the chemical formula $(CH_3C_6H_3NCH_2)_2CH_2$. The Tröger's base, as referred to herein, may be substituted or otherwise functionalized.

As used herein, “anhydride” refers to a moiety of the formula $R_1—C(═O)—O—C(═O)—R_2$, where $R_1$ and $R_2$ are independently alkyl, haloalkyl, aryl, heteroaryl, cycloalkyl, aromatic alkyl, (cycloalkyl)alkyl, and the like.

Aspects of the present disclosure are directed towards a Tröger's base-derived dianhydride (TBDA) as a contorted building block for polyimide-based membranes for gas separation. For this purpose, TBDA was prepared and used to synthesize two solution-processable polyimides using 2,3,5,6-tetramethyl-p-phenylenediamine (TMPD) and 1,7-diamino-6H,12H-5,11-methanodibenzo[1,5]diazocine-2,8-diol (HTB). The polyimides-, TBDA-TMPD and TBDA-HTB, based membranes demonstrated good thermal stability, $CO_2$ permeability, and high gas selectivity. Fresh and aged polyimide-based membranes exhibited differentiated $CO_2$ permeability and gas selectivity. The present polyimide-based membranes provide a new scope for designing high-performance polyimide-bearing nitrogen groups in backbones of structures for varied separation applications.

A Tröger's base (TB) complex having chemical structure I is described. The TB complex has a following chemical formula:

(I)

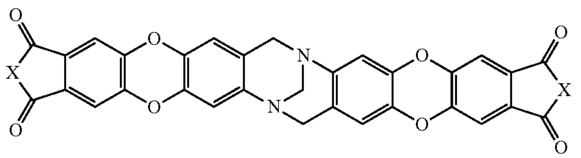

v (TBDA)

The compound of Formula I includes two 'X' where both 'X' may be same or different. In an embodiment, each X is independently selected from O or N—$R_1$. $R_1$ is an aryl group, a substituted aryl group, a heteroaryl group, a Tröger's base compound, or a substituted Tröger's base compound. In a preferred embodiment, 'X' is N—$R_1$. Herein, 'R1' is a comonomer. In an embodiment, a molar ratio of the TB complex of the Formula I to the comonomer is in the range of 1:5 to 5:1, preferably 1:4 to 4:1, preferably 1:3 to 3:1, more preferably 1:2 to 2:1, and yet more preferably about 1:1. The TB complex of the Formula I and the comonomer may be in repeating units. In some embodiments, the repeating units of the TB complex of the Formula I and the comonomer may be in amounts of 1 to 100,000 units, preferably 50 to 80,000 units, preferably 100 to 60,000 units, preferably 1000 to 50,000 units, preferably 5,000 to 40,000 units, preferably 10,000 to 30,000 units, or preferably about 20,000 units. In some embodiments, $R_1$ may be an aryl group. The aryl group may be one or more of a substituted aryl group and non-substituted aryl group. In some embodiments, the aryl group is substituted and may include one or more functional groups and/or substituents. For example, the substituted aryl group may include one or more of hydrogens, halogens, alkyl groups, alkoxy groups, and/or combinations thereof. Examples of suitable halogens may include, among others, one or more of fluorine, chlorine, bromine, and iodine. Examples of suitable alkyl groups may include, among others, one or more of methyl, ethyl, propyl, isopropyl, butyl, iso-butyl, and/or combinations thereof. Examples of suitable alkoxy groups may include, among others, one or more of methoxy, ethoxy, propoxy, butoxy, pentoxy, hexoxy, heptoxy, octoxy, and/or combinations thereof. These shall not be limiting as other substituents disclosed herein can be present or used. In an embodiment, $R_1$ is a substituted aryl group. In a preferred embodiment, the substituted aryl group is a 2,3,5,6-tetramethyl-p-phenylenediamine (TMPD).

In some embodiments, '$R_1$' is a Tröger's base compound. The Tröger's base compound may be substituted or unsubstituted. In some embodiments, the Tröger's base compound is substituted with one or more functional groups and/or substituents such as halogens, alkyl groups, alkoxy groups, combinations thereof, and the like. In a preferred embodiment, $R_1$ is a substituted Tröger's base compound, and the substituted Tröger's base compound is a 1,7-diamino-6H, 12H-5,11-methanodibenzo[1,5]diazocine-2,8-diol (HTB).

A polyimide including the Tröger's base (TB) complex is described. In some embodiments, the polyimide includes repeating units of the TB complex of Formula I, where 'X' is N—$R_1$ and $R_1$ is a substituted aryl group. The substituted aryl group is TMPD. In some embodiments, the polyimide includes repeating units of the TB complex of Formula I, where 'X' is N—$R_1$ and $R_1$ is a substituted Tröger's base compound. The substituted Tröger's base compound is HTB.

FIG. 1A illustrates a flow chart of a method 50 for making the polyimide. The order in which the method 50 is described is not intended to be construed as a limitation, and any number of the described method steps can be combined in any order to implement the method 50. Additionally, individual steps may be removed or skipped from the method 50 without departing from the spirit and scope of the present disclosure.

At step 52, the method 50 includes heating the TB complex of Formula I with a phenol to a first temperature to form a reaction mixture. The TB complex has a following chemical formula:

(I)

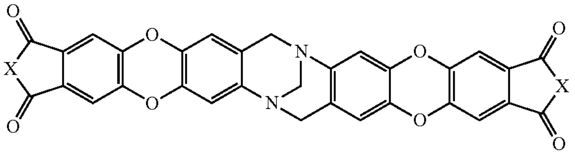

v (TBDA)

The compound of Formula I includes two 'X' where both 'X' may be same or different. In an embodiment, each 'X' is independently selected from O or N—$R_1$. In a preferred embodiment, 'X' is O. The TB complex is heated with a phenol and a catalytic amount of an organic compound containing at least one nitrogen (i.e., the comonomer). The phenol may include phenols and derivatives thereof. For example, in an embodiment, the phenol is a phenol derivative, such as m-cresol, and the phenol derivatives isomers, such as p-cresol and o-cresol. The organic compound containing at least one nitrogen may include a heterocyclic aromatic organic compound. In some embodiments, the organic compound containing at least one nitrogen is quinoline, as well as derivatives and isomers thereof. For example, the organic compound containing at least one nitrogen may be isoquinoline. The heating is preferably carried out in an inert atmosphere. The inert atmosphere may be a nitrogen, xenon, neon, argon, and/or helium atmosphere. The heating is carried out to a temperature range of 80-200° C., preferably 85-150° C., preferably 90-120° C., preferably 95-110° C., and more preferably about 100° C. to form the reaction mixture.

At step 54, the method 50 includes adding a comonomer to the reaction mixture. In an embodiment, the comonomer is 2,3,5,6-tetramethyl-p-phenylenediamine (TMPD). The molar ratio of the TB complex of the Formula I to the TMPD is in the range of 1:5 to 5:1, preferably 1:4 to 4:1, preferably 1:3 to 3:1, more preferably 1:2 to 2:1, and yet more preferably about 1:1. The molar ratio of the TB complex of the Formula I to the comonomer is in the range of 1:5 to 5:1, preferably 1:4 to 4:1, preferably 1:3 to 3:1, more preferably 1:2 to 2:1, and yet more preferably about 1:1.

At step 56, the method 50 includes heating the reaction mixture to a second temperature. In an embodiment, the reaction mixture may be heated under stoichiometric conditions and/or with compounds of high purity. The temperature may range from about room temperature to about 200° C. In many embodiments, the temperature may be gradually increased from a first temperature to one or more other temperatures. For example, the heating may proceed at a first temperature and may be subsequently increased to a second temperature. In an embodiment, the first temperature may be about 50-150° C., preferably 70-130° C., preferably 90-110° C., and more preferably about 100° C., and the second temperature may range from about 150° C. to about 250° C., preferably 160-240° C., preferably 170-230° C., preferably 180-220° C., preferably 190-210° C., and more preferably about 200° C. The duration of the reaction may range from about 1 hour to about 24 hours, preferably 2 to 20 hours, preferably 4 to 18 hours, preferably 6 to 16 hours, preferably 8 to 14 hours, more preferably 10 to 12 hours, and more preferably about 12 hours. In other embodiments, the duration of the reaction may be less than about 1 hour and/or greater than about 24 hours.

At step 58, the method 50 includes precipitating the reaction mixture in a first organic solvent to form a solid. In an embodiment, the first solvent is methanol; optionally other precipitating agents may be used in place of methanol and/or in combination with methanol or the first organic solvent.

At step 60, the method 50 includes precipitating the solid in a second organic solvent to form the polyimide. In some embodiments, the second organic solvent is chloroform; optionally other precipitating agents may be used in place of chloroform and/or in combination with chloroform or the second organic solvent.

At step 62, the method 50 includes drying the polyimide. The polyimide thus formed is dried to a temperature range of 100-150° C., preferably 105-145° C., preferably 110-140° C., preferably 115-130° C., and more preferably about 120° C., for about 18-36 hours, preferably 20-32, preferably 22-26 hours, and more preferably about 24 hours to allow for evaporation of the first organic solvent and the second organic solvent. It is preferred to carry out drying under vacuum to avoid oxidation of the polyimide.

Embodiments of the present disclosure describe membrane films including the polyimides—for example, the membrane films may include and/or may be prepared from any of the TB complexes of Formula I, TBDA-TMPD, and/or TBDA-HTB. The TBDA-HTB-based membrane film includes hydrogen bonds and corresponding polymers made therefrom. The polyimides may be used to fabricate the membrane films, such as thin film composite membranes and/or asymmetric membranes, according to processes and/or methods known in the art. For example, the membrane films may be fabricated by applying a dilute polymer solution containing the Tröger's base polyimides onto a support to form a polyimide coating on a microporous substrate in one step by solvent evaporation. The polyimide coating may be from 1 to 100 coats, preferably 2 to 75 coats, preferably 3 to 50 coats, preferably 4 to 40 coats, preferably 5 to 20 coats, and more preferably about 7 to 15 coats. In another example, the membrane films may be fabricated by one or more of phase separation and phase inversion processes.

In an embodiment, the membrane films may be provided in a variety of geometries, such as flat sheet geometry, a textured (e.g., waves) sheet geometry, a hollow fiber (e.g., cylindrical) geometry, and any geometry known in the art.

The membrane film of the present disclosure demonstrates thermal stability with a decomposition temperature in the range of 410° C. to 440° C., preferably 415 to 435° C., preferably 420 to 430° C., or preferably about 425° C., measured by TGA. In a specific embodiment, the TBDA-TMPD-based membrane has a thermal stability with a decomposition temperature of about 422° C. by TGA. At these temperatures, the carbon content was found to be greater than 90%, preferably 91 to 100%, preferably 92 to 99%, preferably 93 to 98%, preferably 94 to 97%, or preferably 95 to 96%.

The membrane of the present disclosure demonstrates high permeability to $CO_2$. The gas permeability of the TBDA-TMPD-based membrane film lies in the following order: carbon dioxide>hydrogen>oxygen> methane> nitrogen. The gas permeability of the TBDA-HTB-based membrane film is in the following order: hydrogen> carbondioxide>oxygen>nitrogen>methane. In a specific embodiment, the TBDA-TMPD-based membrane has a $CO_2$ permeability coefficient of 1400 barrer to 1500 barrer, preferably 1410 to 1490 barrer, preferably 1420 to 1480 barrer, preferably 1430 to 1470 barrer, preferably 1440 to 1460 barrer, or preferably about 1450 barrer. In an embodiment, the TBDA-HTB-based membrane film has a $CO_2$ permeability coefficient of 60 barrer to 80 barrer, preferably 62 to 78 barrer, preferably 64 to 76 barrer, preferably 66 to 74 barrer, preferably 68 to 72 barrer, or preferably about 70 barrer.

The membrane of the present disclosure also demonstrates high gas selectivity. In a specific embodiment, the TBDA-TMPD-based membrane film has a $CO_2/CH_4$ selectivity of 15 to 25, preferably 16 to 20, preferably 17 to 18, and preferably about 17. In some embodiments, the TBDA-HTB-based membrane film has a $CO_2/CH_4$ selectivity of 30 to 60, preferably 31 to 55, preferably 32 to 50, preferably 33 to 45, preferably 35 to 40, and more preferably about 38. The TBDA-TMPD-based membrane film has a diffusion coefficient of $CO_2$ of $2.0\times10^{-7}$ $cm^2$ $s^{-1}$ to $5.0\times10^{-7}$ $cm^2$ $s^{-1}$, preferably $2.5\times10^{-7}$ to $4.5\times10^{-7}$ $cm^2$ $s^{-1}$, preferably $3.0\times10^{-7}$ to $4.0\times10^{-7}$ $cm^2$ $s^{-1}$, or preferably about $3.5\times10^{-7}$ $cm^2$ $s^{-1}$. The TBDA-HTB-based membrane film has a diffusion coefficient of $CO_2$ of $2.0\times10^{-8}$ $cm^2$ $s^{-1}$ to $3.0\times10^{-1}$ $cm^2$ $s^{-1}$, preferably $2.2\times10^{-7}$ to $2.8\times10^{-7}$ $cm^2$ $s^{-1}$, or preferably about $2.4\times10^{-7}$ to $2.6\times10^{-7}$ $cm^2$ $s^{-1}$. The TBDA-TMPD-based membrane film after aging for 80 days to 100 days, preferably 85 to 95 days, preferably about 90 days, has a higher $H_2/N_2$, $H_2/CH_4$, $O_2/N_2$, and $CO_2/CH_4$ selectivity compared to the membrane film before the aging. The TBDA-HTB-based membrane film after aging for 40 days to 60 days, preferably 45 to 55 days, or preferably about 50 days, the membrane film has a higher $H_2/N_2$, $H_2/CH_4$, $O_2/N_2$, and $CO_2/CH_4$ selectivity compared to the membrane film before the aging.

EXAMPLES

The following examples demonstrate a Tröger's base-derived dianhydride as a contorted building block for polyimide-based membranes for gas separation. The examples are provided solely for illustration and are not to be construed as limitations of the present disclosure, as many variations thereof are possible without departing from the spirit and scope of the present disclosure.

Example 1: Materials 2,3,5,6-Tetramethyl-p-phenylenediamine (TMPD, 97%), 3,4-dimethoxyaniline (98%), paraformaldehyde ($(CH_2O)_n$, 95%), trifluoroacetic acid ($CF_3COOH$, 99%), boron tribromide ($BBr_3$, 99.9%), 4,5-dichlorophthalonitrile (99%), m-cresol (99%), isoquinoline (97%), acetic anhydride ($(CH_3CO)_2O$, 98%), dichloromethane (DCM, 99%), N,N-dimethylformamide (DMF, 98.8%), chloroform ($CHCl_3$, 99%), 1-methyl-2-pyrrolidone (NMP, 99.5%), potassium carbonate ($K_2CO_3$, 99%), magnesium sulfate ($MgSO_4$, 97%), potassium hydroxide (KOH, >85%), hydrochloric acid (HCl, 37%), methanol (MeOH, 99%), and ethanol (99%) were purchased from Merck and used without further purification. 1,7-Diamino-6H,12H-5,11-methanodibenzo[1,5]diazocine-2,8-diol (HTB, 98%) was prepared as previously reported [X. Ma, M. Abdulhamid, X. Miao, I. Pinnau, Facile Synthesis of a Hydroxyl-Functionalized Tröger's Base Diamine: A New Building Block for High-Performance Polyimide Gas Separation Membranes, *Macromolecules*. 50 (2017) 9569-9576, incorporated herein by reference in its entirety].

Example 2: Characterization $^1H$ NMR spectra of all intermediates (i-v) were obtained from Bruker AVANCE-III spectrometer at 400 MHz in deuterated dimethyl sulfoxide (DMSO-$d_6$). High-resolution mass spectroscopy (HR-MS) analysis of compounds iii, iv, and v were obtained from Thermo LC/MS system with LTQ Orbitrap Velos detectors. Thermal gravimetric analysis (TGA) was conducted on TGA Q5000 under an inert atmosphere with a heating rate of 5° C. $min^{-1}$. Fourier-transform infrared (FTIR) spectra of the polyimides was acquired using a Thermo Fisher Scientific Nicolet spectrometer (iS10) with a wave number range of 525 $cm^{-1}$ to 4000 $cm^{-1}$. Polymer molecular weight ($M_w$ and $M_n$) and polydispersity index were measured using gel permeation chromatography (GPC) in an Agilent 1200 system. The measurements were performed in dimethylformamide (DMF) using polystyrene reference. The geometric density of the membranes was measured using film thickness, weight data, and area. The hydrogen bonding detection and fractional free volume were conducted by molecular dynamic simulation using Materials Studio 8.0 and Chemaxon software, respectively.

Example 3: Synthesis of Polymer 2,3,8,9-tetramethoxy-6H,12H-5,11-methanodibenzo[b,f][1,5]diazocine (i)

3,4-Dimethoxyaniline (6 g, 39.2 mmol) and paraformaldehyde (1.88 g, 62.7 mmol) were added to the round bottom flask and cooled to −20° C., followed by dropwise addition of $CF_3COOH$ (120 ml). The reaction was stirred at room temperature for 48 hours and poured into cooled water (200 ml). The product was extracted using dichloromethane, dried, and concentrated using rota-evaporation. White powder (6 g, 89%) was gained after silica gel column separation using petroleum ether/dichloromethane: 3/7 as eluent. $^1H$ NMR (400 MHz, DMSO-$d_6$): δ 3.64 (s, 6H), 3.72 (s, 6H), 3.99-4.03 (d, 2H, J=16.4 Hz), 4.13 (s, 2H), 4.45-4.49 (d, 2H, J=16.4 Hz), 6.49 (s, 2H), 6.67 (s, 2H).

Example 4: Synthesis of Polymer 6H,12H-5,11-methanodibenzo[b,f][1,5]diazocine-2,3,8,9-tetraol (ii)

A solution of intermediate i (2.24 g, 6.54 mmol) in dry dichloromethane was cooled to zero degrees, followed by slow addition of $BBr_3$ (6.3 mL, 65.4 mmol). The reaction was stirred for 2 hours at zero degrees and left to stir overnight at room temperature. The reaction was poured onto 50 mL of cooled water, and the pH was adjusted between 4-5 by adding sodium bicarbonate. The obtained precipitates were filtered and desiccated in the oven at 70° C. under vacuum for 24 hours to achieve an off-white solid (1.0 g, 73% yield). $^1H$ NMR (400 MHz, DMSO-$d_6$): δ 3.72-3.76 (d, 2H, J=16 Hz), 4.01 (s, 2H), 4.31-4.35 (d, 2H, J=16 Hz), 6.25 (s, 2H), 6.42 (s, 2H), 8.57 (s, 2H), 8.75 (s, 2H).

Example 5: Synthesis of 8H,18H-7,17-methanobenzo[5',6'][1,4]dioxino[2',3':4,5]benzo[1,2-b]benzo[5',6'][1,4]dioxino[2',3':4,5]benzo[1,2-f][1,5]diazocine-2,3,12,13-tetracarbonitrile (iii)

To a round bottom flask containing intermediate ii (0.94 g, 3.28 mmol) and 4,5-dichlorophtalonitrile (1.42 g, 7.22 mmol), 50 mL of dry DMF was added. The reaction medium was heated to 80° C. for 15 minutes before adding potassium carbonate ($K_2CO_3$) (2.8 g, 20 mmol), which was added in portions over 5 minutes. The system was stirred overnight and then cooled down to room temperature, and the obtained precipitation was filtered and washed a few times with distilled water and acetone. The white product was then collected and refluxed with dichloromethane (DCM) for 10 hours, filtrated, and dried in the vacuum oven overnight at 120° C. The desired product was obtained as an off-white solid (1.5 g, 86% yield). $^1H$ NMR (400 MHz, DMSO-$d_6$): δ 4.02 (d, 2H, J=16 Hz), 4.15 (s, 2H), 4.45 (d, 2H, J=16 Hz), 6.68 (s, 2H), 6.82 (s, 2H), 7.74 (s, 4H). HR-MS for [$M+H^+$, $C_{31}H_{15}N_6O_4^+$, ESI]: Calcd: 535.1077; Found: 535.1149.

Example 6: The Synthesis of 8H,18H-7,17-methanobenzo[5',6'][1,4]dioxino[2',3':4,5]benzo[1,2-b]benzo[5',6'][1,4]dioxino[2',3':4,5]benzo[1,2-f][1,5]diazocine-2,3,12,13-tetracarbonitrile (iv)

A solution of KOH (1.75 g, 31 mmol, 8 mL) was added gradually to a dispersion of intermediate iii (0.5 g, 0.935 mmol) in ethanol (8 mL). The reaction was heated to reflux overnight. The clear solution was concentrated in the rotary evaporator, and precipitates were obtained after adding distilled water and HCl (6 M, 2.6 mL). An off-white product was obtained upon HCl addition; the powder was filtered and washed a few times with diluted HCl (1 M). The product was dried for 18 hours in the vacuum oven at 40° C. then washed again with water to eradicate any salt traces. The desired product was obtained after drying as a yellow solid (0.486 g, 85%). $^1H$ NMR (400 MHz, DMSO-$d_6$): δ 3.99-4.03 (d, 2H, J=17 Hz), 4.14 (s, 2H), 4.43-4.47 (d, 2H, J=17 Hz), 6.62 (s, 2H), 6.76 (s, 2H), 7.16 (s, 2H), 7.17 (s, 2H). HR-MS for [$M+H^+$, $C_{31}H_{19}N_2O_{12}^+$, ESI]: Calcd: 611.0860; Found: 611.0932.

Example 7: The Synthesis of Tröger's Base-Based Dianhydride (TBDA) (v)

Intermediate iv (0.45 g, 0.74 mmol) was suspended in 20 mL acetic anhydride. The reaction medium was heated to 120° C. and left to stir overnight. The precipitated solid was filtered and washed three times with acetic anhydride. The product (0.4 g, 95% yield) was gained after vacuum drying at 140° C. for 12 h. $^1$H NMR (400 MHz, DMSO-$d_6$): δ 4.04 (d, 2H, J=17 Hz), 4.16 (s, 2H), 4.46 (d, 2H, J=17 Hz), 6.66 (s, 2H), 6.7 (s, 2H), 7.63 (m, 4H). HR-MS [$M+H^+$, $C_{31}H_{15}N_2O_{10}^+$, ESI]: Calcd: 575.0648; Found: 575.0721.

Example 8: The Synthesis of TBDA-HTB and TBDA-TMPD Polyimides

TBDA (97 mg, 0.17 mmol) and HTB (48 mg, 0.17 mmol) or TMPD (29 mg, 0.17 mmol) were placed in a two-neck round bottom flask equipped with a nitrogen inlet and oil bubbler. 2 mL of m-cresol was added to the round bottom flask, and the reaction was heated to 100° C., where 0.1 mL of isoquinoline was added, followed by gradual heating to 200° C. The solution was precipitated into methanol to achieve fiber-like polymers. Re-precipitation of the polymers from their N-methyl-2-pyrrolidone (NMP) and chloroform solutions for TBDA-HTB and TBDA-TMPD, respectively, was conducted to remove any impurities. 93% to 95% yield was obtained after collecting the polymers from the vacuum oven which was heated at 120° C. for 24 hours. TBDA-HTB: FTIR (v, $cm^{-1}$): 3000-3680 (—OH), 2830-2990 (—CH), 1776 (asym, C═O), 1706 (sym, C═O), 1354 (C—N); ρ=1.38 g $cm^{-3}$; FFV=0.12. TBDA-TMPD: FTIR (v, $cm^{-1}$): 2830-3000 (—CH), 1774 (asym, C═O), 1708 (sym, C═O), 1352 (C—N); $M_w$=57,115 g $mol^{-1}$, M=37,429 g $mol^{-1}$, PDI=1.52. ρ=1.21 g $cm^{-3}$; FFV=0.20.

Example 9: Dense Film Preparation

TBDA-HTB and TBDA-TMPD polymers were dissolved in NMP and chloroform (2% to 3% w/v), respectively, and the solutions were filtered through 0.45 μm PTFE filters and poured into flat glass Petri dishes. The TBDA-HTB solution was placed in the oven at 60° C. to slowly evaporate NMP under $N_2$ flow, while the TBDA-TMPD membrane was attained from deliberate evaporation of chloroform at room temperature. The two flexible membranes were desiccated in the oven at 120° C. and 250° C. for TBDA-TMPD and TBDA-HTB, respectively, for 24 hours to ensure the total removal of any solvent residual.

Example 10: Gas Permeation Measurements

The gas permeability of Tröger's base-based polyimides membranes was measured by the constant-volume/variable-pressure method. TBDA-HTB and TBDA-TMPD were degassed in the permeation box for 24 hours at 35° C. before starting measurements. All gases were tested at 2 bar and 35° C., and permeability was calculated based on the following equation:

$$P = D * S = 10^{10}\left(\frac{VL}{ARTp_{up}}\right)\left(\frac{dp}{dt}\right)$$

where P is the gas permeability in barrer [1 barrer=$10^{-10}$ $cm^3$ (STP) cm $cm^{-2}$ $s^{-1}$ $cmHg^{-1}$)], V is the calibrated permeate volume ($cm^3$), L is the membrane thickness (cm), A is the effective membrane area ($cm^2$), R is the gas constant (0.278 $cm^3$ cmHg $cm^{-3}$ (STP) $K^{-1}$), T is the operating temperature (K), $p_{up}$ refers to upstream pressure (cmHg) and dp/dt represent the equilibrium permeate-side pressure increase (cmHg $s^{-1}$). The selectivity was determined from the permeability ratio of the gases, that is, $\alpha=P_A/P_B$.

Figure 1B:
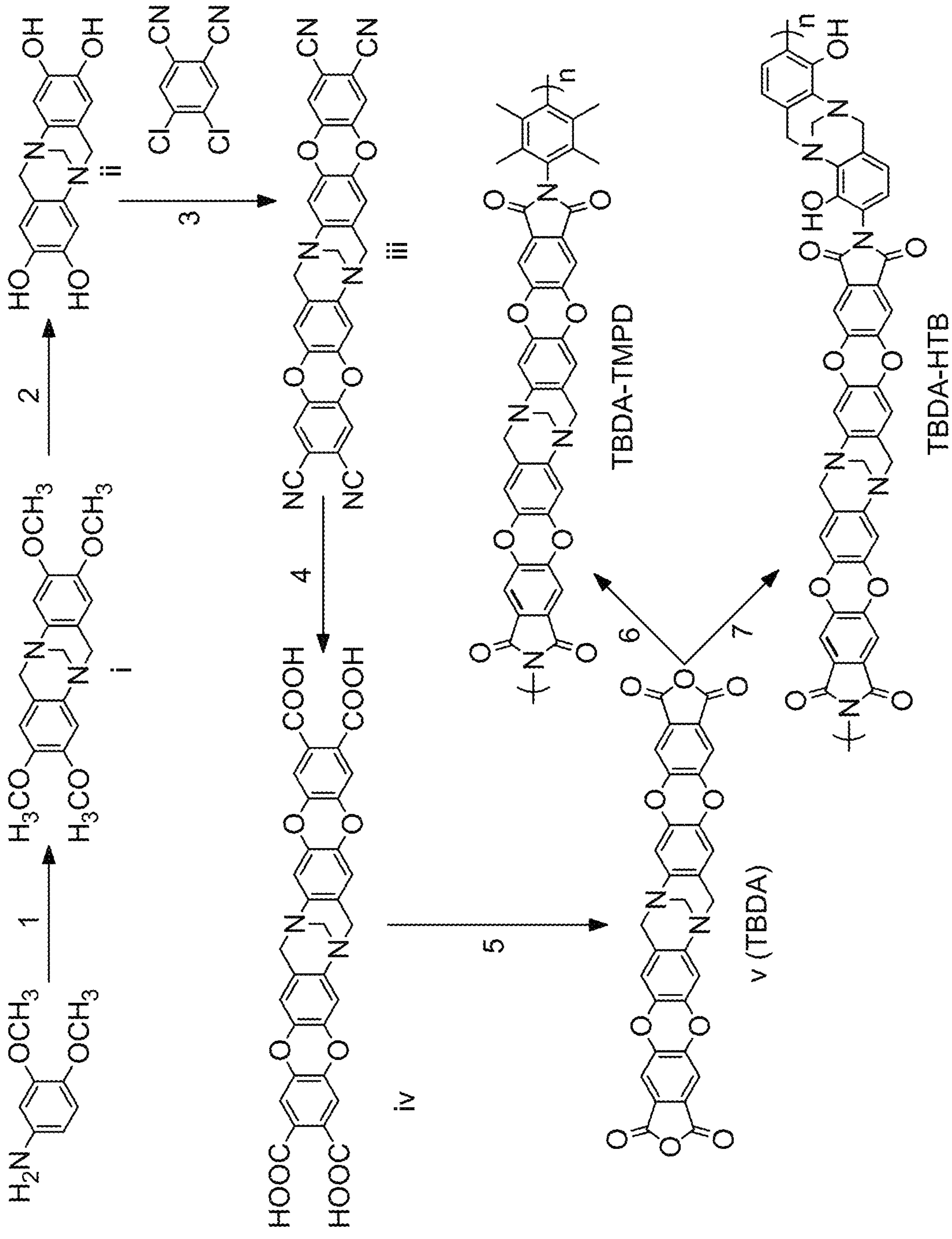
FIG. 1B is a schematic illustration of Tröger's base-based dianhydride (TBDA) and its corresponding polyimides, according to certain embodiments.

Referring to FIG. 1B, a schematic illustration depicting the synthesis of Tröger's base-based dianhydride (TBDA) and its corresponding polyimides, is illustrated. In FIG. 1B, 1=$(CH_2O)_n$, $CF_3COOH$, −20° C.; 2=DCM, $BBr_3$, 0° C.; 3=$K_2CO_3$, 80° C.; 4=KOH, EtOH, reflux; 5=$(CH_3CO)_2O$, 120° C.; 6=2,3,5,6-Tetramethyl-p-phenylenediamine (TMPD), m-cresol, isoquinoline, 200° C.; 7=1,7-Diamino-6H,12H-5,11-methanodibenzo[1,5]diazocine-2,8-diol (HTB), m-cresol, isoquinoline, 200° C.

Tröger's base-based dianhydride (TBDA, v) was synthesized in five synthetic steps. Firstly, 3,4-dimethoxyaniline was reacted with paraformaldehyde in $CF_3COOH$ to form intermediate i as Tröger's base containing four methoxy groups. The methoxy groups in intermediate i are all converted into hydroxyl groups using $BBr_3$ to achieve intermediate ii. Secondly, intermediate ii was reacted with 4,5-dichlorophthalonitrile through nucleophilic aromatic substitution reaction to produce intermediate iii. Further, the hydrolysis of intermediate iii was conducted using a KOH/water/ethanol system to convert cyano groups (CN) to carboxylic acid groups (COOH), resulting in intermediate iv. Furthermore, the conversion of tetracarboxylic acid to dianhydride was conducted by refluxing intermediate iv with acetic anhydride, resulting in the final product v.

Figure 2A:
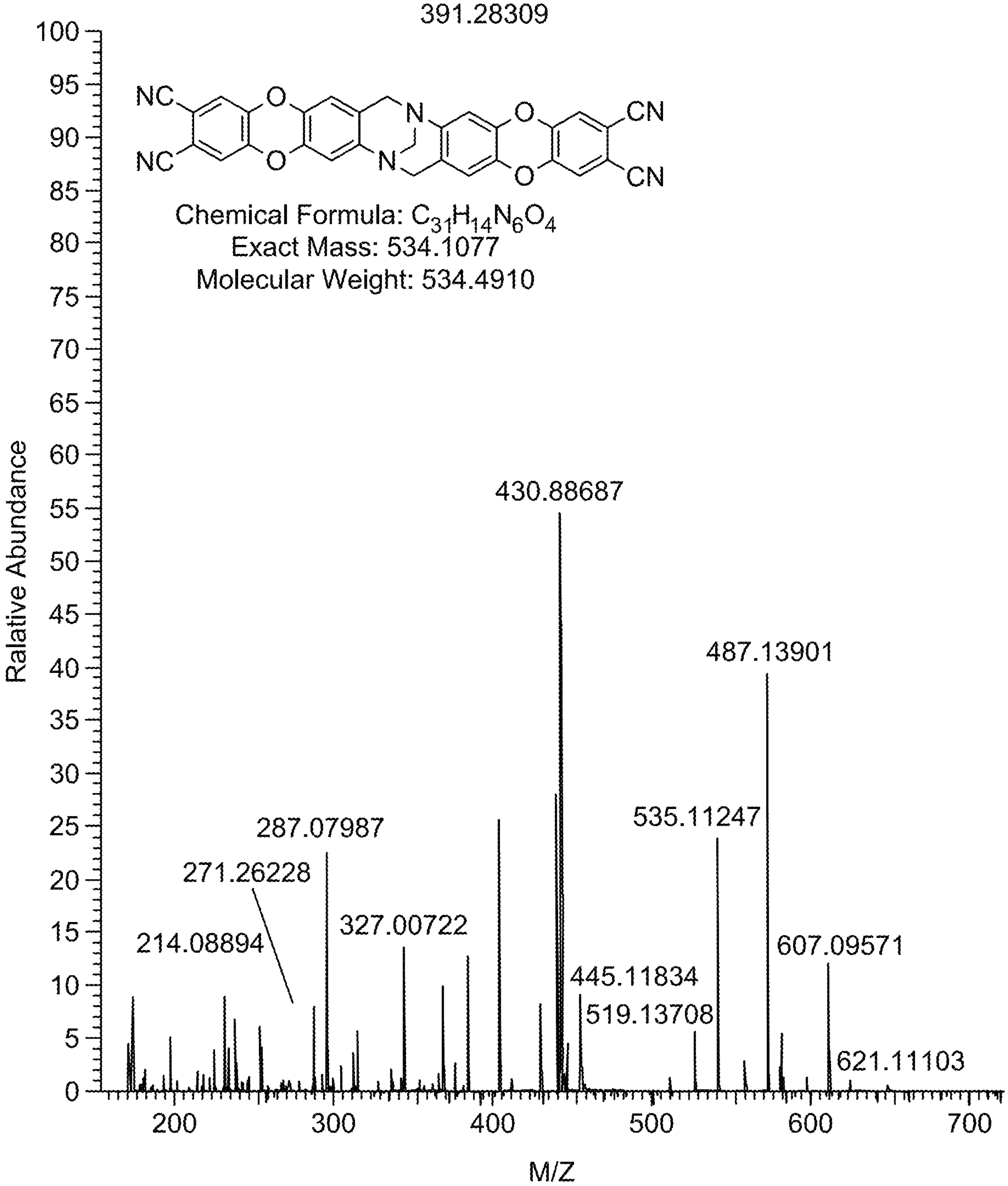
FIGS. 2A-2C depict high-resolution mass spectroscopy (HRMS) spectra for TBDA-dianhydride intermediates, according to certain embodiments.
Figure 2B:
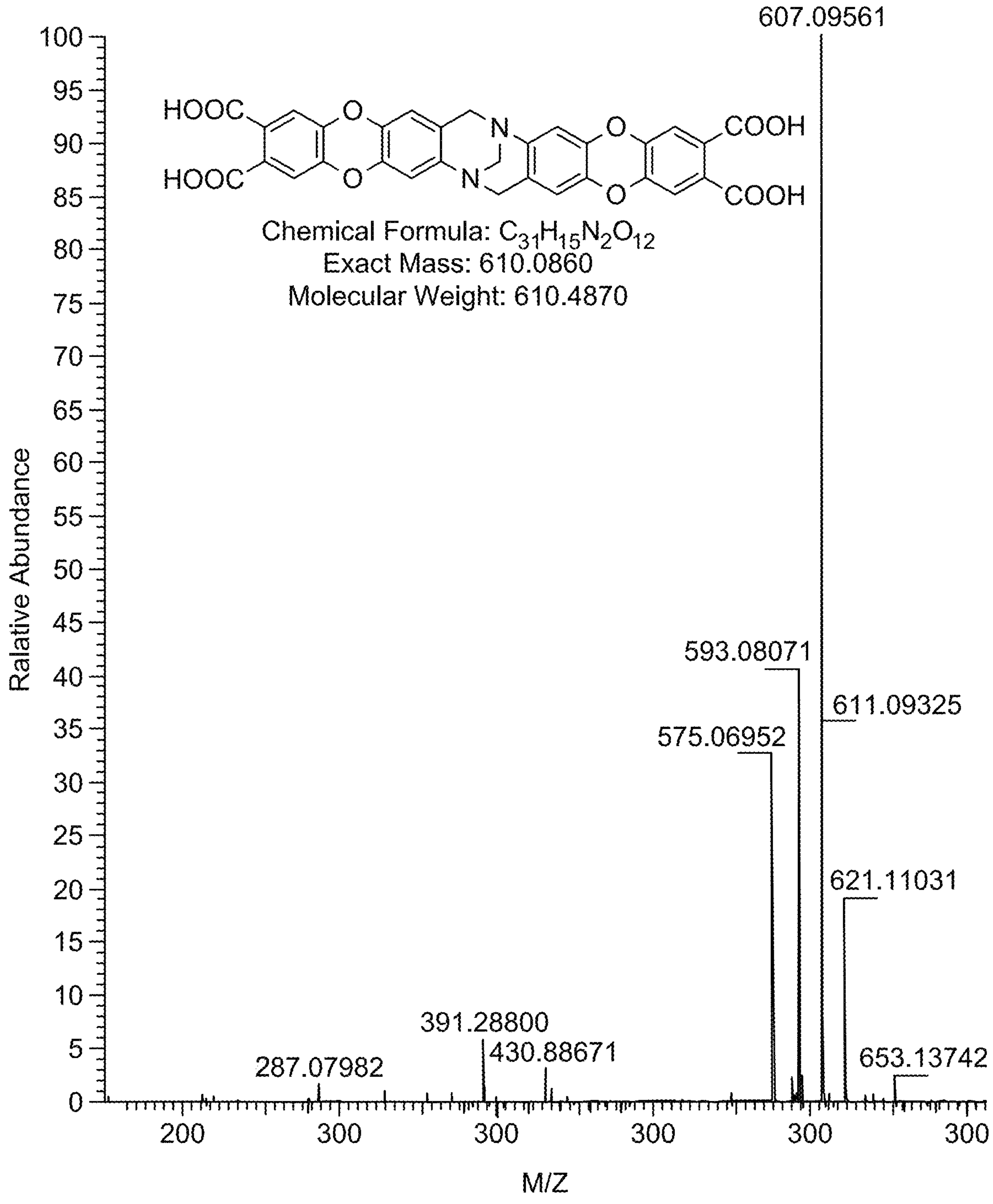
Figure 2C:
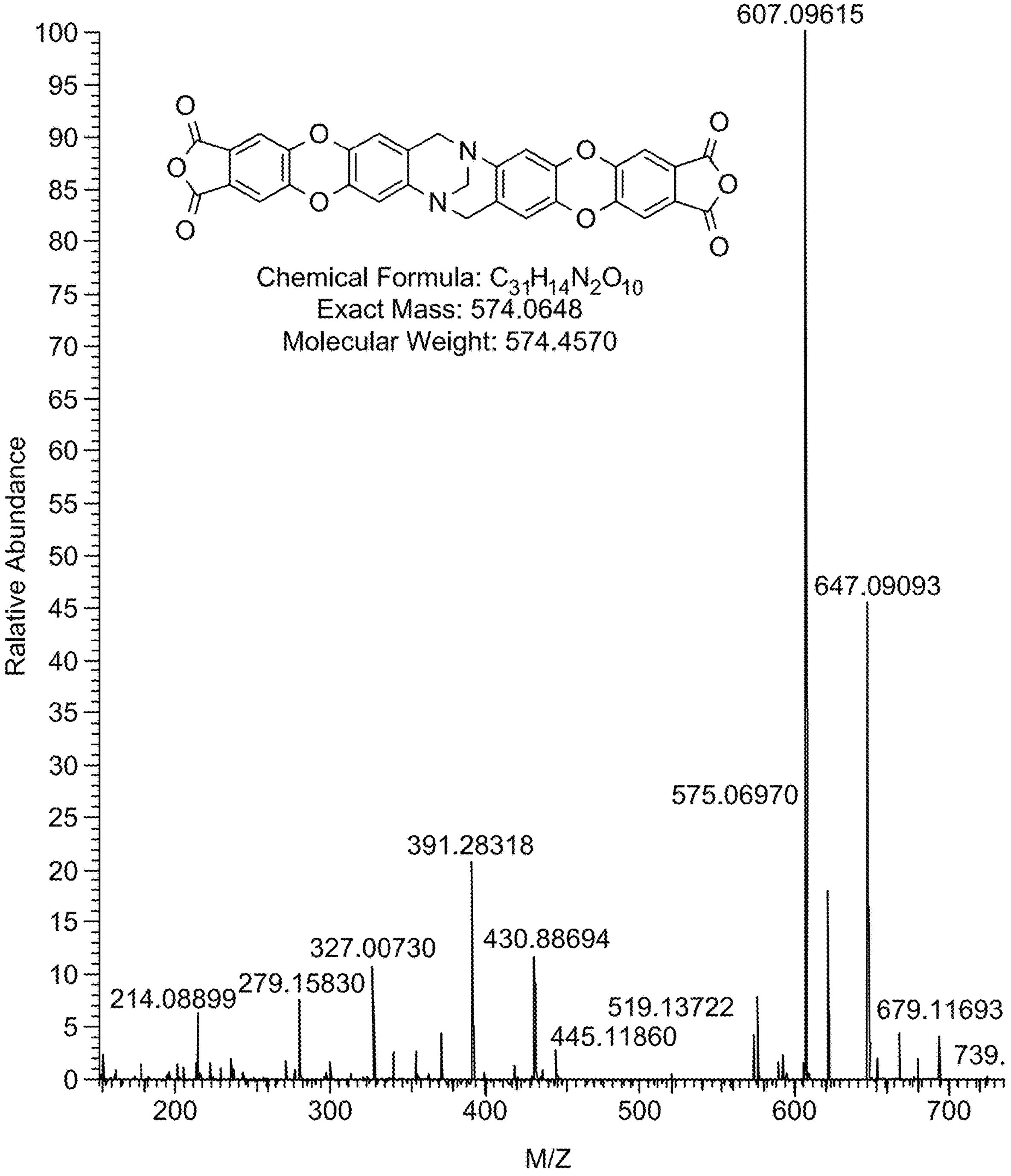

Referring to FIGS. 2A-2C, a high-resolution mass spectroscopy (HR-MS) spectrum of TBDA intermediates [iii-v] is illustrated. The chemical structure of all intermediates and the final product was confirmed by $^1$H NMR. Further, the exact molecular weight of compounds iii, iv, and v were confirmed by the HR-MS as depicted in FIGS. 2A-2C.

Figure 3:
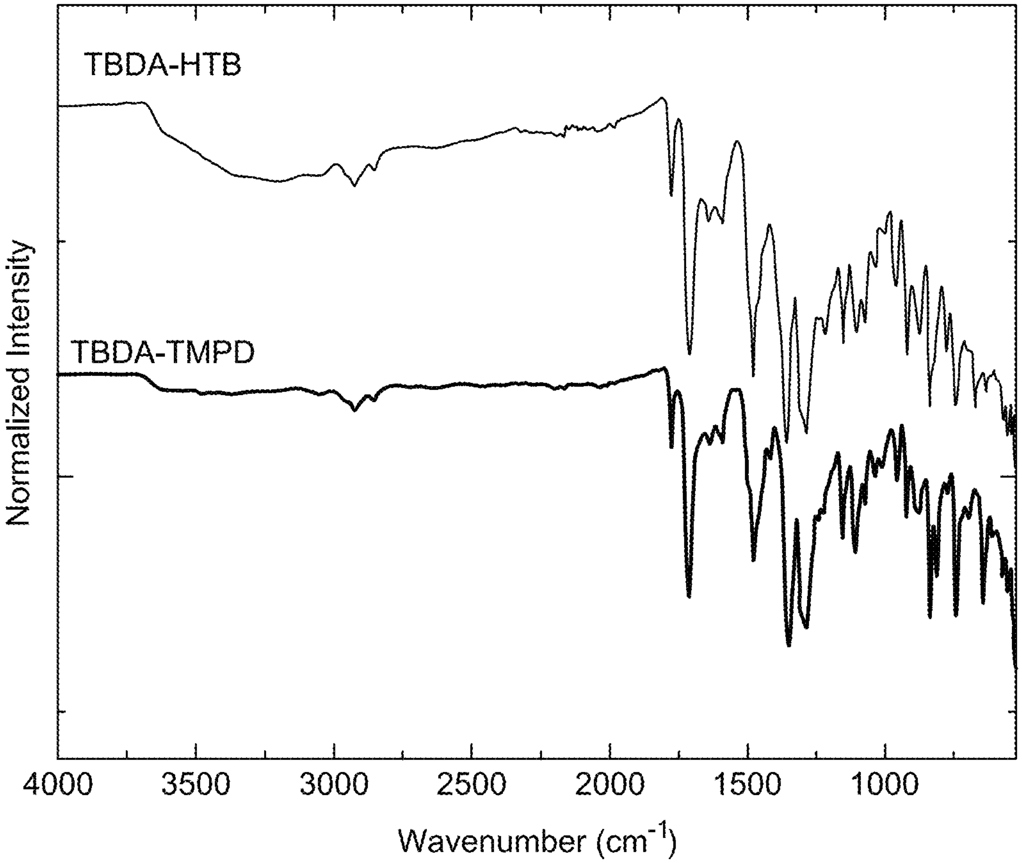
FIG. 3 depicts Fourier transform infrared (FTIR) spectra of TBDA-based polyimides in a range of 525 $cm^{-1}$ to 4000 $cm^{-1}$, according to certain embodiments.

Referring to FIG. 3, FTIR spectra of the TBDA-based polyimides in the range of 525 $cm^{-1}$ to 4000 $cm^{-1}$ is illustrated. TBDA-HTB and TBDA-TMPD polyimides were prepared using the polycondensation reaction [X. Ma, M. Abdulhamid, I. Pinnau, Design and Synthesis of Polyimides Based on Carbocyclic Pseudo-Tröger's Base-Derived Dianhydrides for Membrane Gas Separation Applications, *Macromolecules.* 50 (2017) 5850-5857, incorporated herein by reference in its entirety]. An equimolar amount of the dianhydride (TBDA) and the diamines (i.e., HTB and TMPD) were added to a Schlenk tube containing m-cresol under continuous nitrogen flow. The reaction was heated gradually up to 200° C. to ensure full imidization of polyamic acid to polyimide. The complete conversion to polyimide was confirmed by FTIR, where the absorption bands of the asymmetric and symmetric stretching of C═O were detected at 1776 $cm^{-1}$ and 1706 $cm^{-1}$, respectively. The —OH band of TBDA-HTB was detected in the range of 3000 $cm^{-1}$ to 3682 $cm^{-1}$, while the C—N band was found at 1354 $cm^{-1}$.

Both polyimides displayed different solubility behavior in organic solvents due to the difference in functionalities on their backbone. For instance, TBDA-TMPD demonstrated good solubility in chlorinated solvents, such as dichloromethane (DCM), chloroform ($CHCl_3$), and polar aprotic solvents, as shown in Table 1, due to the presence of four methyl groups which helps to increase solubility. However, TBDA-HTB displayed bad solubility, where it was only soluble in NMP and m-cresol at room temperature.

TABLE 1

TBDA-based polyimide solubility in different solvents.

| Polymer | DCM | $CHCl_3$ | Acetone | THF | DMF | DMSO | NMP | m-cresol |
|---|---|---|---|---|---|---|---|---|
| TBDA-HTB | -- | -- | -- | -- | -- | -- | ++ | ++ |
| TBDA-TMPD | ++ | ++ | -- | ++ | ++ | ++ | ++ | ++ |

Not soluble is represented by '--' and soluble is represented by '++'.

Figure 4:
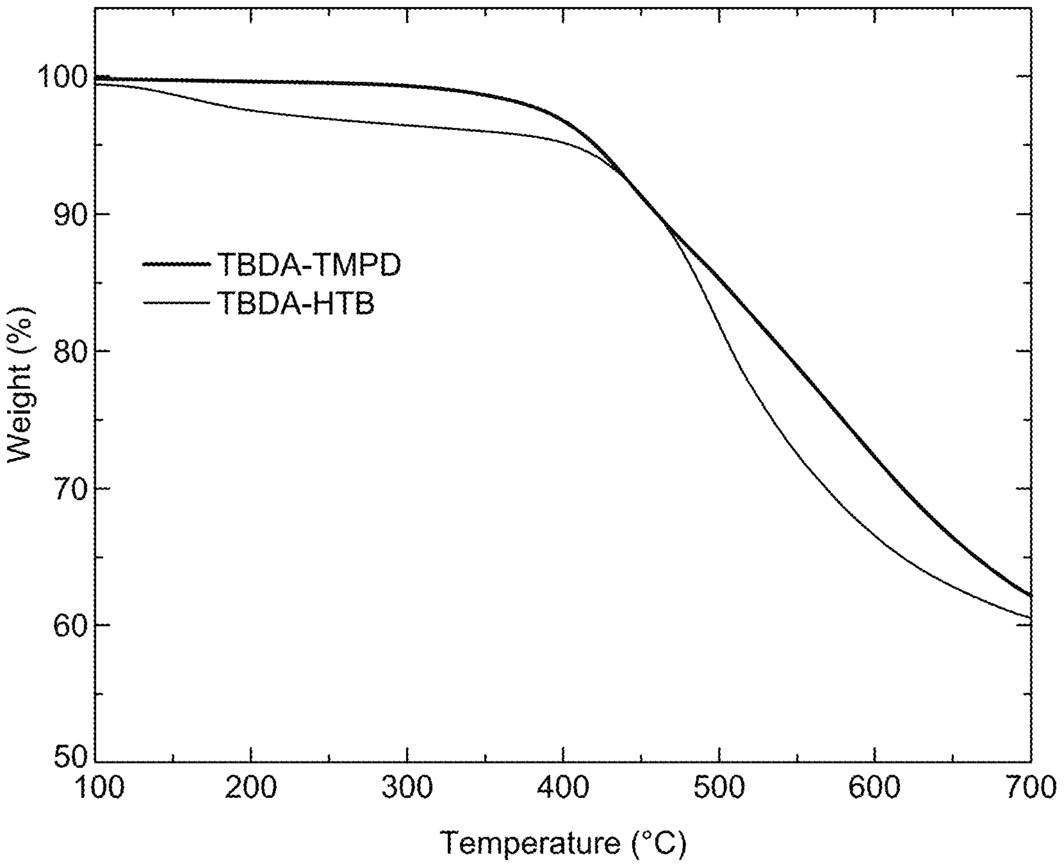
FIG. 4 depicts thermogravimetric analysis (TGA) of TBDA-HTB and TBDA-TMPD in the range of 100° C. to 700° C., according to certain embodiments.

Referring to FIG. 4, the thermogravimetric analysis of TBDA-HTB and TBDA-TMPD, in the range of 100° C. to 700° C., is illustrated. As can be seen from FIG. 4, the thermal stability of the obtained polyimides was evaluated by thermal gravimetric analysis (TGA) under a nitrogen atmosphere. Both polymers displayed high decomposition temperatures with $T_{d,5\%}$ of 422° C. and 400° C. for TBDA-TMPD and TBDA-HTB, respectively. Moreover, both polyimides displayed high carbon content upon thermal carbonization, as shown in Table 2.

TABLE 2

The carbon content of TBDA-HTB and TBDA-TMPD at different temperatures.

| Polymer | 400° C. | 500° C. | 600° C. | 700° C. |
|---|---|---|---|---|
| TBDA-TMPD | 97% | 85% | 72% | 62% |
| TBDA-HTB | 95% | 81.7% | 66.4% | 60.5% |

TBDA-HTB revealed lower thermal stability and carbon content at all temperatures relative to TBDA-TMPD. This lower stability could be attributed to the earlier degradation of—OH groups on polymer chains of TBDA-HTB. Nonetheless, both polymers showed carbon content of approximately 60% at 700° C. indicating that these polymers can be good contenders to fabricate carbon-based membranes for gas separation applications.

Figure 5A:
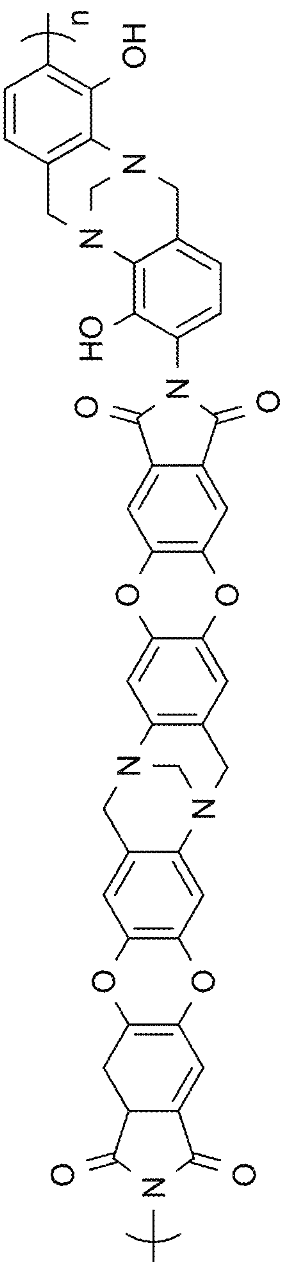
FIG. 5A is a pictorial representation depicting the three-dimensional structure of TBDA-HTB after energy optimization, according to certain embodiments.
Figure 5A:
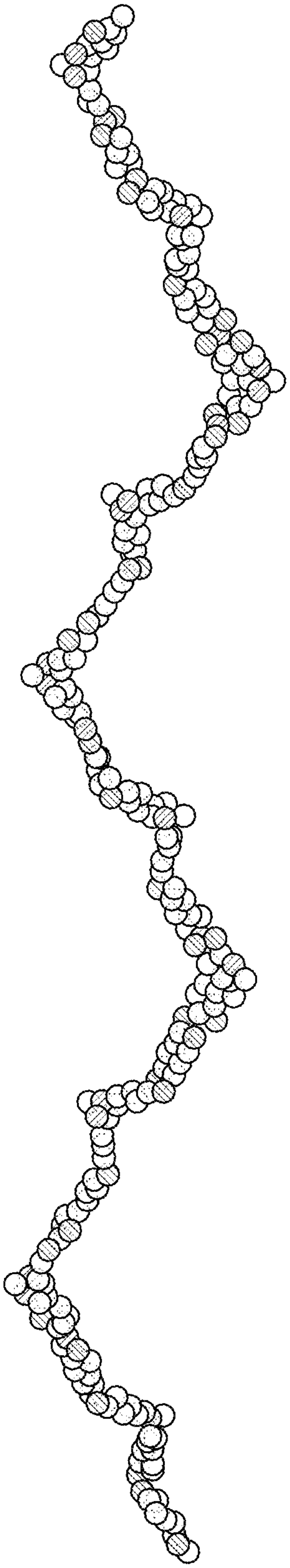
Figure 5B:
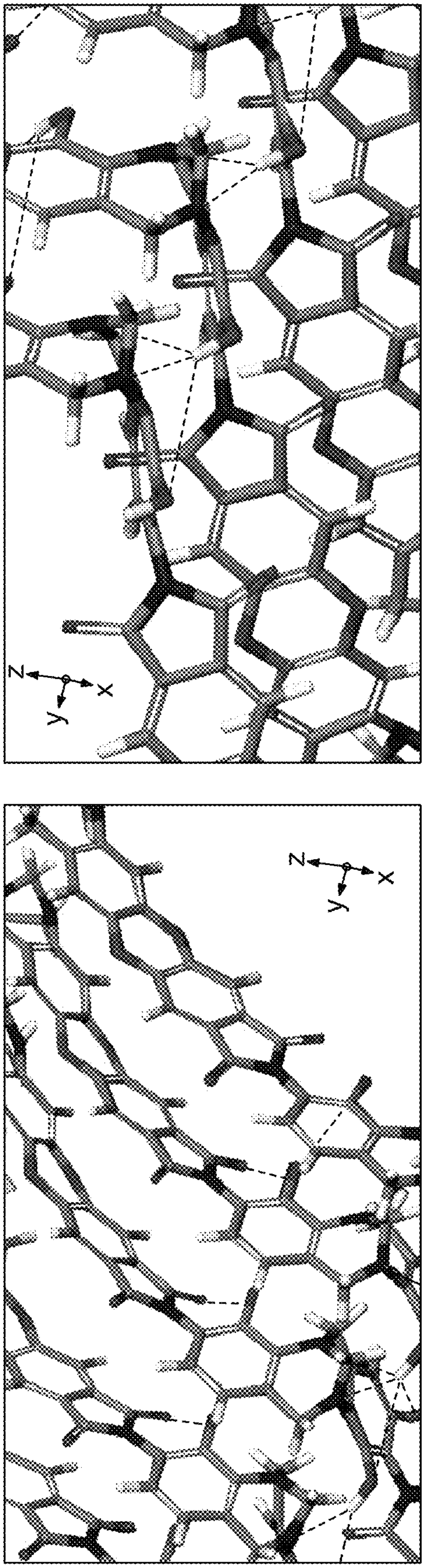
FIG. 5B is a pictorial representation depicting hydrogen bonding interactions in TBDA-HTB as observed by molecular dynamic simulation, according to certain embodiments.

Referring to FIG. 5A, a three-dimensional structure of TBDA-HTB after energy optimization is illustrated. The permeabilities of TBDA-HTB follow the sequence $H_2>CO_2>O_2>N_2>CH_4$ [X. Ma, M. Abdulhamid, X. Miao, I. Pinnau, Facile Synthesis of a Hydroxyl-Functionalized Tröger's Base Diamine: A New Building Block for High-Performance Polyimide Gas Separation Membranes, *Macromolecules*. 50 (2017) 9569-9576, incorporated herein by reference in its entirety]. However, the permeabilities of TBDA-TMPD follow a different sequence: $CO_2>H_2>O_2>CH_4>N_2$. This difference in trends could be attributed to porosity. Referring to FIG. 5B, a pictorial representation of hydrogen bonding interactions of TBDA-HTB as observed from molecular dynamic simulation is illustrated. In the case of TBDA-HTB, the presence of —OH groups can lead to hydrogen bond formation with different accepting groups, such as C═O and C—N—C, which results in a tighter structure, better molecular sieving properties, and a higher permeability selectivity. In the case of TBDA-TMPD, however, the presence of methyl groups ortho to the imide linkage restricts efficient packing between polymer chains, resulting in a looser membrane with high permeability and moderate selectivity [M. A. Abdulhamid, X. Ma, X. Miao, I. Pinnau, Synthesis and characterization of a microporous 6FDA-polyimide made from a novel carbocyclic pseudo Tröger's base diamine: Effect of bicyclic bridge on gas transport properties, Polymer (Guildf); and M. A. Abdulhamid, H. W. H. Lai, Y. Wang, Z. Jin, Y. C. Teo, X. Ma, I. Pinnau, Y. Xia, Microporous Polyimides from Ladder Diamines Synthesized by Facile Catalytic Arene-Norbornene Annulation as High-Performance Membranes for Gas Separation, Chem, both of which are incorporated herein by reference in their entireties]. TBDA-TMPD demonstrated higher gas permeability and selectivity relative to 6FDA-TMPD. For instance, TBDA-TMPD displayed $CO_2$ permeability of 1457 barrer, which is three-fold higher than the $CO_2$ permeability obtained from 6FDA-TMPD, with $CO_2/CH_4$ selectivity of 17. Moreover, the fresh sample of TBDA-TMPD revealed $O_2$ permeability of 291 barrer, which is two-fold higher than the permeability obtained from 6FDA-TMPD, and $O_2/N_2$ selectivity of 3.9. Although both polyimides (i.e., 6FDA-TMPD and TBDA-TMPD) were prepared using the same diamine (TMPD) and different dianhydrides (TBDA and 6FDA), TBDA-TMPD showed better performance, indicating that TBDA is a good alternative to 6FDA dianhydride. Furthermore, the gas separation performance of TBDA-TMPD exceeded the performance obtained from PIM-PI-1, with a higher permeability and selectivity for all tested gases. Furthermore, membranes prepared from TBDA-HTB displayed higher gas selectivity relative to membranes prepared from TBDA-TMPD. For instance, fresh TBDA-HTB displayed a $CO_2/CH_4$ selectivity of 38, which is two-fold higher than the selectivity observed from TBDA-TMPD. Moreover, TBDA-HTB revealed an $O_2/N_2$ selectivity of 5.3 which is 36% higher than the selectivity obtained from TBDA-TMPD. TBDA-HTB also exhibited an $H_2/CH_4$ selectivity of 88, which is six-fold higher than the selectivity resulted from TBDA-TMPD. The higher selectivity resulted from TBDA-HTB is attributed to the presence of hydroxyl functional groups on the polymer backbone [N. Alaslai, X. Ma, B. Ghanem, Y. Wang, F. Alghunaimi, I. Pinnau, Synthesis and Characterization of a Novel Microporous Dihydroxyl-Functionalized Triptycene-Diamine-Based Polyimide for Natural Gas Membrane Separation, *Macromol. Rapid Commun*; and S. L. Li, Z. Zhu, J. Li, Y. Hu, X. Ma, Synthesis and gas separation properties of OH-functionalized Tröger's base-based PIMs derived from 1,1'-binaphthalene-2,2'-OH, Polymer (Guildf), both of which are incorporated herein by reference in their entireties].

The gas separation performance of the aged TBDA-TMPD membrane, which was evaluated after 90 days of physical aging, demonstrated approximately 50% reduction in permeability with 6 to 17% enhancement in gas-pair selectivity. This reduction in permeability and marginal improvement in selectivity is attributed to the physical aging of polymer chains in porous polymers that shrinks pore size and reduce its free volume [R. Swaidan, B. Ghanem, E. Litwiller, I. Pinnau, Physical Aging, Plasticization and Their Effects on Gas Permeation in "rigid" Polymers of Intrinsic Microporosity, *Macromolecules*, which is incorporated herein by reference in its entirety]. The pure gas measurements of fresh and aged TBDA-HTB and TBDA-TMPD are displayed in Table 3.

TABLE 3

Pure gas permeability and selectivity of TBDA-HTB and TBDA-TMPD measured at 35 ° C. and 2 bar.

| | Permeability (barrer) | | | | | Ideal selectivity ($\alpha_{X/Y}$) | | | |
|---|---|---|---|---|---|---|---|---|---|
| Polymer | $H_2$ | $N_2$ | $O_2$ | $CH_4$ | $CO_2$ | $H_2/N_2$ | $H_2/CH_4$ | $O_2/N_2$ | $CO_2/CH_4$ |
| TBDA-HTB (29 μm)[a] | 162 | 2.7 | 14.3 | 1.8 | 71 | 60 | 88 | 5.3 | 38 |
| TBDA-HTB aged 50 days | 147 | 1.98 | 12.1 | 1.14 | 61 | 74 | 129 | 6.1 | 54 |
| TBDA-TMPD (45 μm)[b] | 1283 | 73.7 | 291 | 85.7 | 1457 | 17 | 15 | 3.9 | 17 |
| TBDA-TMPD aged 90 days | 623 | 34 | 141 | 38 | 744 | 18 | 16 | 4.1 | 20 |

[a]membrane was treated at 250° C.;
[b]membrane was treated at 120° C.

Figure 5C:
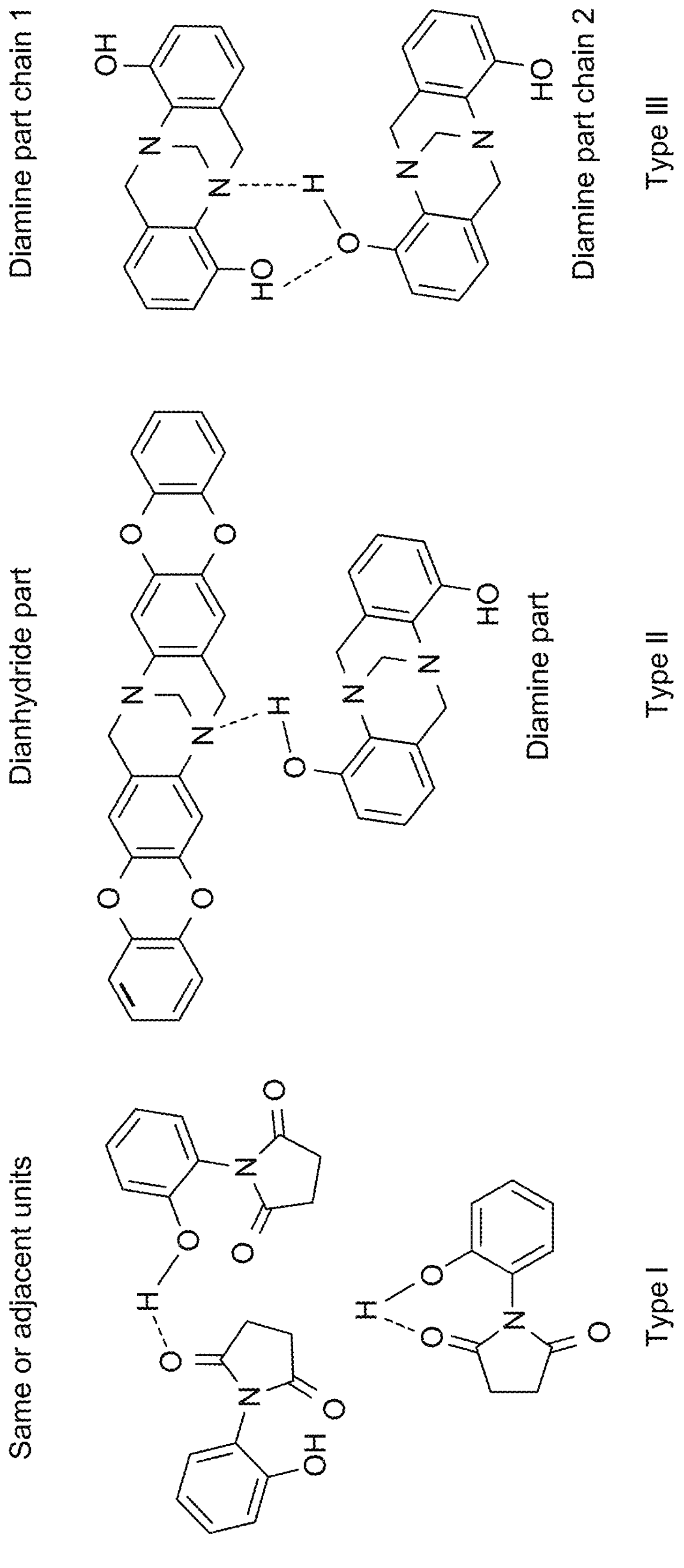
FIG. 5C is a pictorial representation depicting type I, type II, and type III hydrogen bonding occurrence in a polymer matrix, according to certain embodiments.

Referring to FIG. 5C, a pictorial representation depicting type I, type II, and type III hydrogen bonding occurrence in a polymer matrix is illustrated. TBDA-HTB exhibited higher gas-pair selectivity relative to TBDA-TMDP due to the presence of hydrogen bonding that tightens the pores and increases the size-sieving properties of the membranes. As can be seen from FIG. 5C, a few possible hydrogen bonding interactions may happen within the polymer matrix, as detected by molecular dynamic simulation. For instance, there is a possibility for hydrogen bonding formation between the —OH group and the C═O of the imide group in the same or adjacent units (Type I). Type II hydrogen bonding reflects the potential H-bonding between the —OH from HTB and the tertiary amine of Tröger's base-based dianhydride unit. Type III hydrogen bonding imitates the H-bonding between two polymer chains. A combination of all possible hydrogen bonds leads to strong chain tightening and better size-sieving properties. The fresh sample of TBDA-HTB displayed $CO_2$ permeability of 71 barrer, which is 29% higher than the permeability obtained from the 30-day aged sample of 6FDA-HTB (55 barrer) [X. Ma, M. Abdulhamid, X. Miao, I. Pinnau, Facile Synthesis of a Hydroxyl-Functionalized Tröger's Base Diamine: A New Building Block for High-Performance Polyimide Gas Separation Membranes, *Macromolecules.* 50 (2017) 9569-9576, incorporated herein by reference in its entirety]. Further, the 50-days physically aged TBDA-HTB membrane led to a marginal reduction (14%) in $CO_2$ permeability (from 71 to 61 barrer) and a 42% improvement in $CO_2/CH_4$ selectivity (from 38 to 54). Additionally, an enhancement in $H_2/CH_4$ selectivity (47%) was observed after 50 days of aging, along with a 9% reduction in $H_2$ permeability.

Furthermore, the low reduction rate in TBDA-HTB indicates a tight structure that is less affected by aging relative to the more open structure of TBDA-TMPD, which showed an about 50% reduction in permeabilities. The low reduction rate was ascribed to the strong hydrogen bond interaction [N. Alaslai, B. Ghanem, F. Alghunaimi, E. Litwiller, I. Pinnau, Pure- and mixed-gas permeation properties of highly selective and plasticization resistant hydroxyl-diamine-based 6FDA polyimides for $CO_2/CH_4$ separation, *J. Memb. Sci.* 505 (2016) 100-107, incorporated herein by reference in its entirety].

Furthermore, the TBDA-TMPD displayed higher diffusion coefficients than TBDA-HTB, as shown in Table 4. This reflects the higher gas permeability of TBDA-TMPD. Further, TBDA-HTB demonstrated higher solubility coefficients for $O_2$ and $N_2$ relative to TBDA-TMPD. Pure-gas diffusion and solubility coefficients of $CO_2$, $CH_4$, $O_2$, and $N_2$ are illustrated in Table 4.

TABLE 4

Pure-gas diffusion and solubility coefficients of $CO_2$, $CH_4$, $O_2$, and $N_2$ for fresh and aged samples of TBDA-TMPD and TBDA-HTB at 2 atm and 35° C., based on the time-lag method.

| | Diffusion coefficient ($10^{-8}$ $cm^2$ $s^{-1}$)[a] | | | | Solubility coefficient ($10^{-2}$ $cm^3$ (STP) $cm^{-1}$ $cmHg^{-1}$)[b] | | | |
|---|---|---|---|---|---|---|---|---|
| Polymer | $CO_2$ | $CH_4$ | $O_2$ | $N_2$ | $CO_2$ | $CH_4$ | $O_2$ | $N_2$ |
| TBDA-TMPD-fresh | 42.8 | 12.4 | 94 | 38 | 34.1 | 6.91 | 3.1 | 1.95 |
| TBDA-TMPD-aged (90 days) | 24.1 | 6.95 | 65 | 23.1 | 30.9 | 5.46 | 2.17 | 1.48 |
| TBDA-HTB-fresh | 2.17 | 0.28 | 2.8 | 0.54 | 32.5 | 6.6 | 5.13 | 4.97 |
| TBDA-HTB-aged (50 days) | 2.02 | 0.20 | 2.49 | 0.43 | 30.3 | 5.6 | 4.87 | 4.58 |

The denomination '[a]' is determined by the time lag method;
'[b]' calculated from S = P/D.

TBDA-HTB revealed a higher diffusion selectivity coefficient relative to TBDA-TMPD, which exceeded two-fold, indicating a higher gas-pair selectivity in TBDA-HTB. The aforementioned diffusion selectivity is illustrated in Table 5. This increase in diffusion selectivity of TBDA-HTB is attributed to the tighter chain packing induced by the presence of tertiary amine and a hydroxyl group [M. A. Abdulhamid, X. Ma, X. Miao, I. Pinnau, Synthesis and characterization of a microporous 6FDA-polyimide made from a novel carbocyclic pseudo Tröger's base diamine: Effect of bicyclic bridge on gas transport properties, Polymer (Guildf), incorporated herein by reference in its entirety]. Further, aged samples of both polymers demonstrated marginal improvement in solubility selectivity.

TABLE 5

$CO_2/CH_4$ and $O_2/N_2$ diffusion selectivity and solubility selectivity for TBDA-TMPD and TBDA-HTB (T = 35° C., P = 2 bar).

| | Diffusion selectivity $(\alpha)_D$ | | Solubility selectivity $(\alpha)_S$ | |
|---|---|---|---|---|
| Polymer | $CO_2/CH_4$ | $O_2/N_2$ | $CO_2/CH_4$ | $O_2/N_2$ |
| TBDA-TMPD-fresh | 3.45 | 2.47 | 4.9 | 1.58 |
| TBDA-TMPD-aged (90 days) | 3.46 | 2.81 | 5.6 | 1.46 |
| TBDA-HTB-fresh | 7.75 | 5.2 | 4.9 | 1.03 |
| TBDA-HTB-aged (50 days) | 10.1 | 5.8 | 5.4 | 1.06 |

No changes in diffusion selectivity of TBDA-TMPD were noted after aging; however, differences in diffusion selectivity were observed for the aged sample of TBDA-HTB, which increased by about 30% upon physical aging. This increase in diffusion selectivity reflects the 42% increase in $CO_2/CH_4$ after 50 days of aging.

Referring to FIGS. 6A-6D, permeability and selectivity performance upper bound plots for TBDA-based polyimides for $CO_2/CH_4$, $H_2/CH_4$, $H_2/N_2$, and $O_2/N_2$ gas pairs, respectively, are illustrated. As can be seen from FIG. 6A, TBDA-based polyimides generally demonstrated higher performance relative to commercial and other polyimide-based membranes. For instance, the fresh membrane of TBDA-TMPD displayed higher $CO_2$ permeability and $CO_2/CH_4$ selectivity compared to 6FDA-TMPD and PIM-PI-1, which were prepared from the same diamine (TMPD) but different contorted dianhydrides, such as 6FDA and spirobisindane. Further, as can be seen from FIGS. 6B-6C, fresh membranes of TBDA-TMPD and TBDA-HTB made it to 2008 upper bound for $H_2/CH_4$ separation, indicating the potential of TBDA-based membranes for high separation performance. Furthermore, TBDA-HTB demonstrated higher gas permeability with comparable, or even higher, gas selectivity for all tested gas pairs relative to commercial membranes such as cellulose acetate, polysulfone, and Matrimid.

Figure 6A:
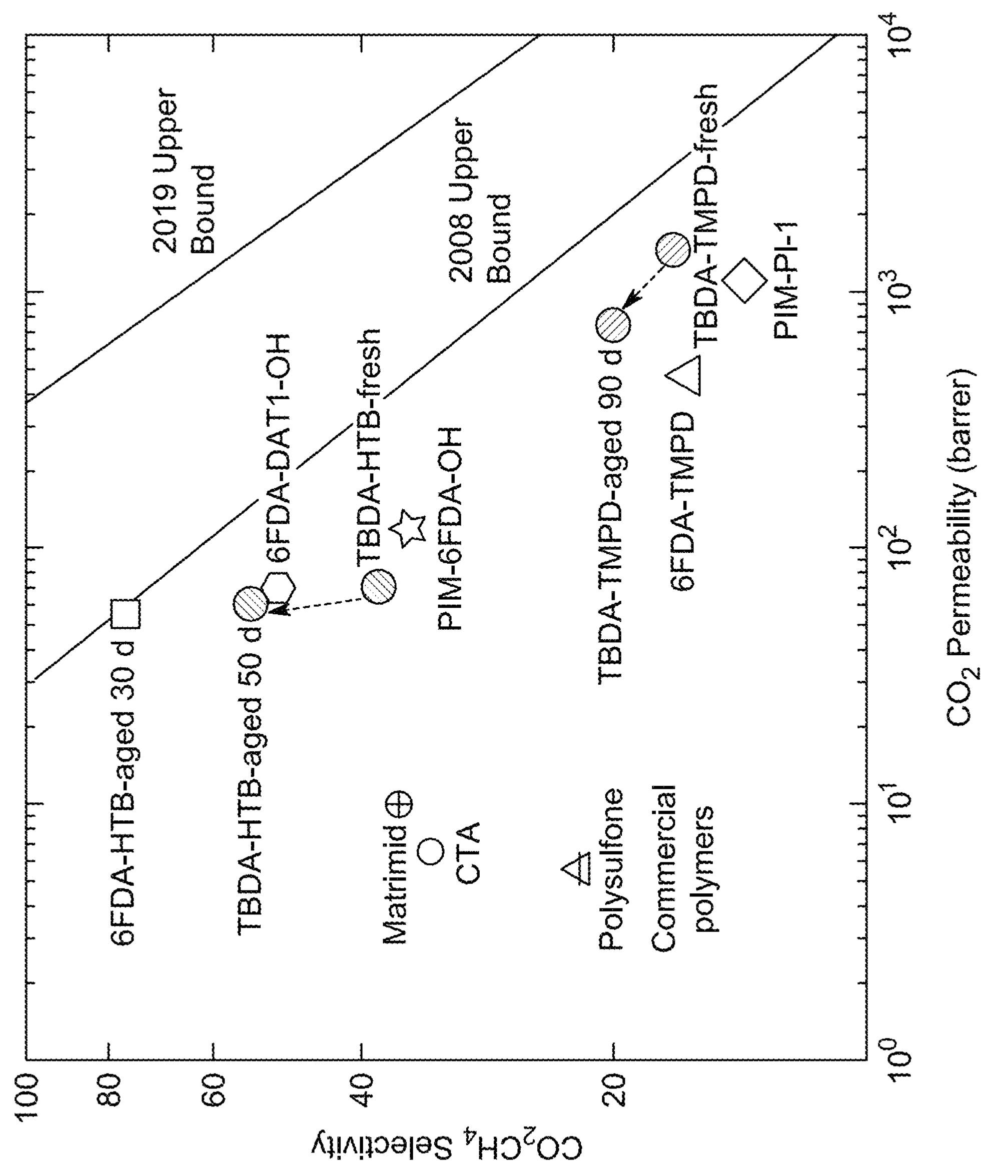
FIG. 6A is a graph depicting permeability and selectivity performance upper bound plots for TBDA-based polyimides of $CO_2/CH_4$ gas pair, according to certain embodiments.
Figure 6B:
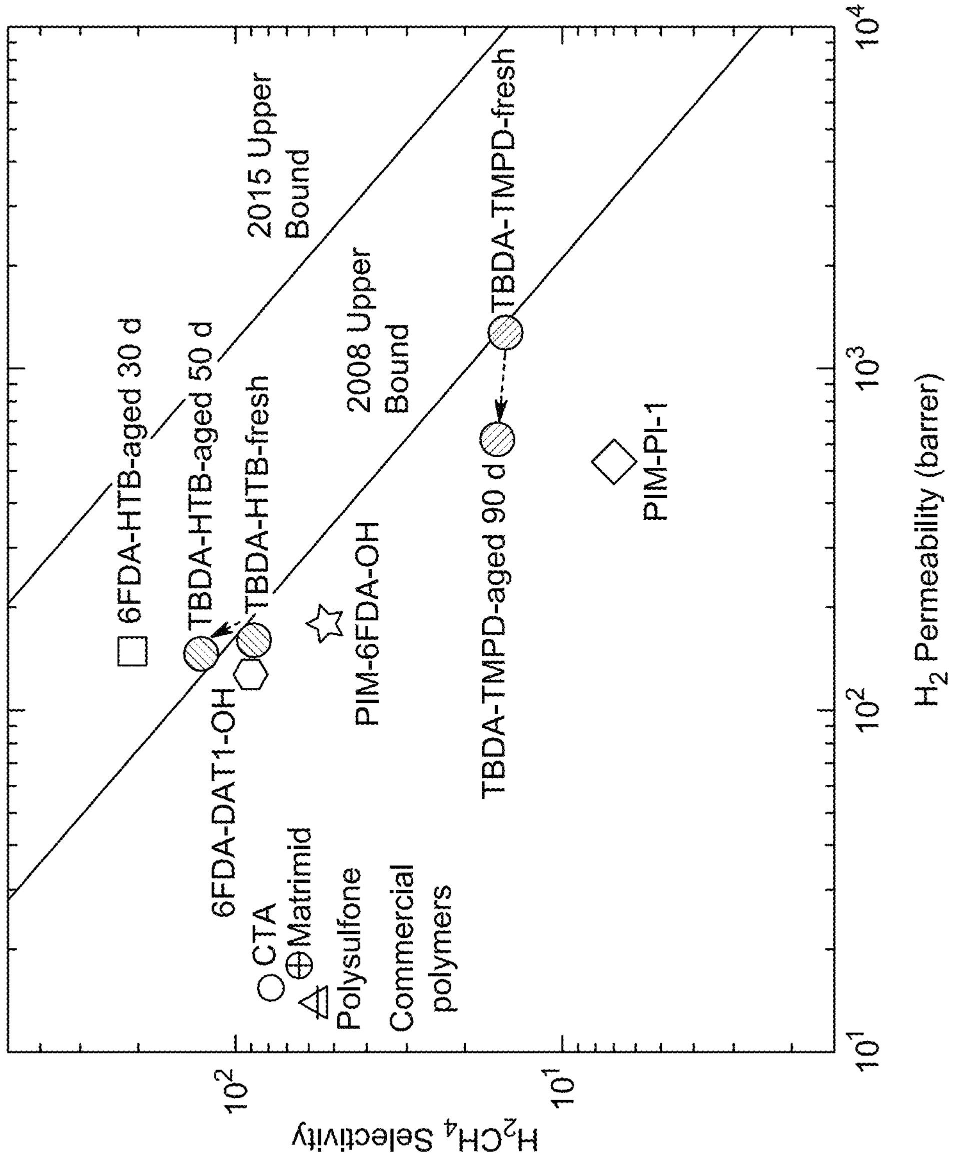
FIG. 6B is a graph depicting permeability and selectivity performance upper bound plots for TBDA-based polyimides of $H_2/CH_4$ gas pair, according to certain embodiments.
Figure 6C:
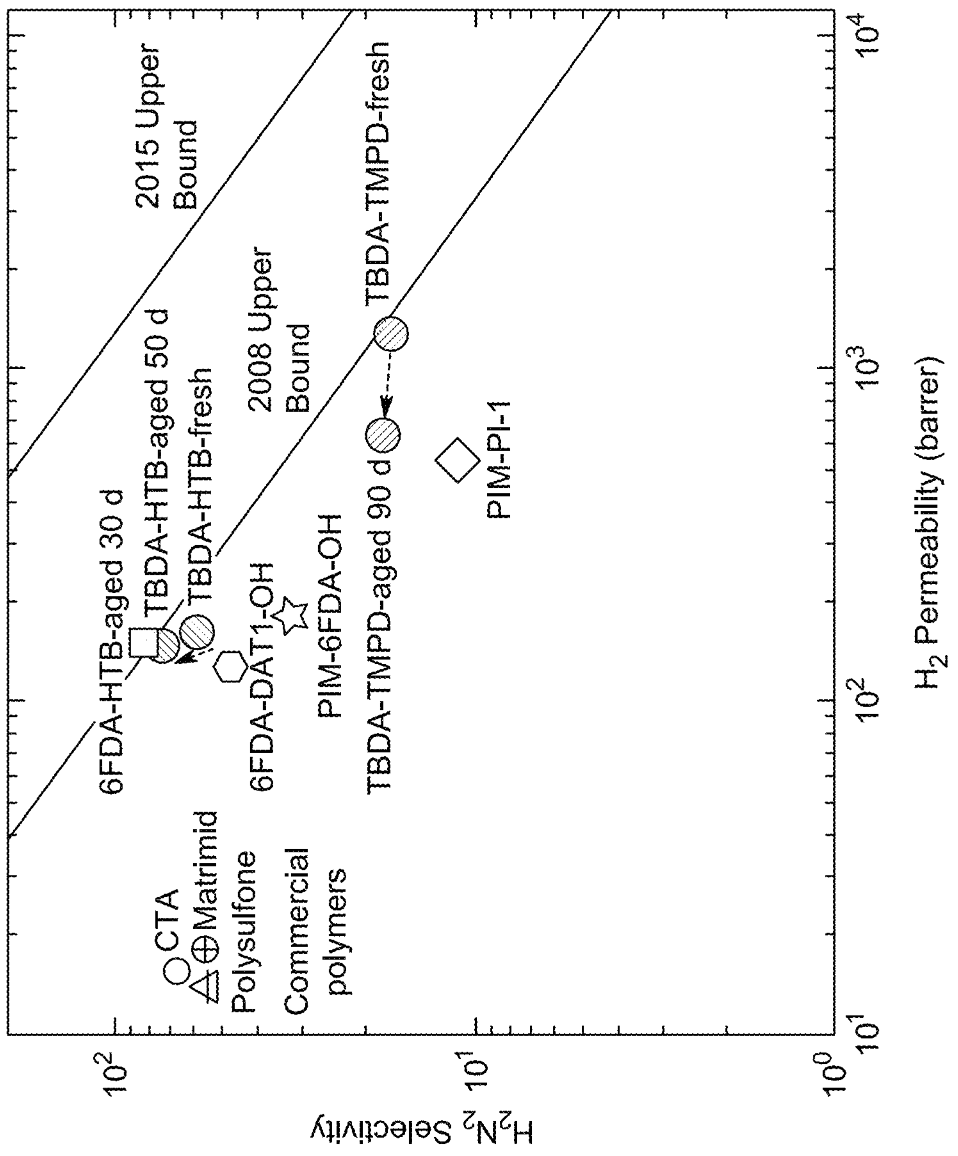
FIG. 6C is a graph depicting permeability and selectivity performance upper bound plots for TBDA-based polyimides of $H_2/N_2$ gas pair, according to certain embodiments.
Figure 6D:
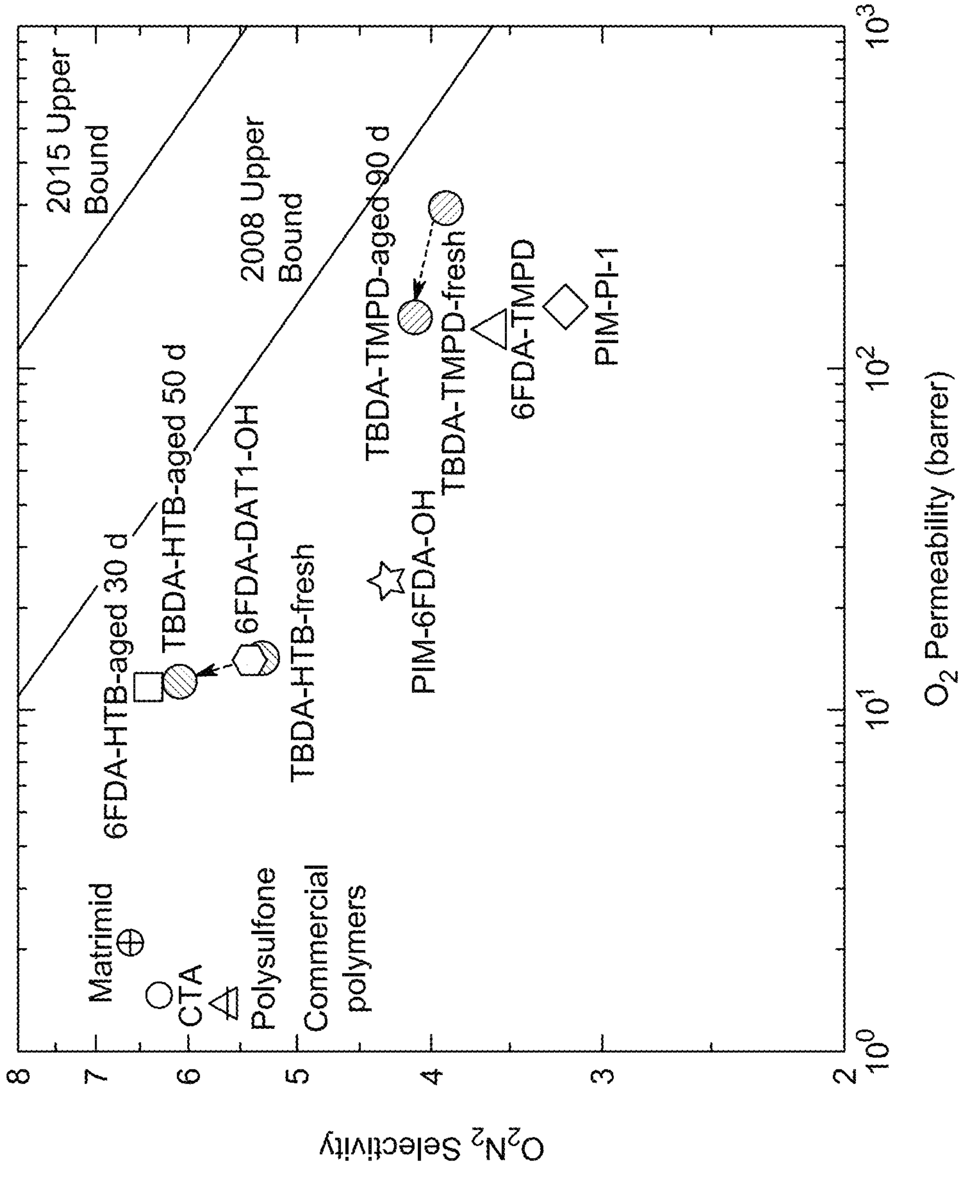
FIG. 6D is a graph depicting permeability and selectivity performance upper bound plots for TBDA-based polyimides of $O_2/N_2$ gas pair, according to certain embodiments.

As can be seen from FIG. 6D, the aged film of TBDA-HTB displayed $O_2$ permeability of about 12 barrer, which is seven times higher than the permeability in cellulose triacetate (CTA) with the same $O_2/N_2$ selectivity. The present disclosure demonstrates that Tröger's base-based dianhydride is a promising building block for synthesizing and developing high-performance polyimides for membrane-based gas separation.

A Tröger's base-based dianhydride (TBDA) was synthesized and characterized. Two TBDA-based polyimides were prepared from polycondensation reactions using two different diamines (i.e., TMPD and HTB). The TBDA-based polyimides demonstrated thermal stability at temperatures exceeding 400° C. TBDA-TMPD displayed higher permeability and selectivity for all tested gases relative to 6FDA-TMPD. Hydroxyl-functionalized TBDA-HTB showed a balanced combination between gas permeability and selectivity with $CO_2$ permeability of 61 and $CO_2/CH_4$ selectivity of 55. The TBDA-TMPD membrane displayed $CO_2$ permeability of 1457 barrer and $CO_2/CH_4$ selectivity of 17. Physical aging over 50 days of TBDA-HTB membrane revealed $CO_2$ permeability of 61 barrer and $CO_2/CH_4$ selectivity of 54. Aged TBDA-HTB exhibited a performance that crossed 2008 upper bound for $H_2/CH_4$ separation with an $H_2$ permeability of 147 barrer and an $H_2/CH_4$ selectivity of 129. The high gas-pair selectivity for TBDA-HTB is attributed to different hydrogen bonding interactions among the polymer chains. Developing contorted dianhydride provides scope for designing high-performance polyimide-bearing nitrogen groups in their backbones for different separation applications.

Numerous modifications and variations of the present disclosure are possible in light of the above teachings. It is therefore to be understood that within the scope of the appended claims, the present disclosure may be practiced otherwise than as specifically described herein.

The invention claimed is:

1. A Tröger's base (TB) complex having chemical structure I:

(I)

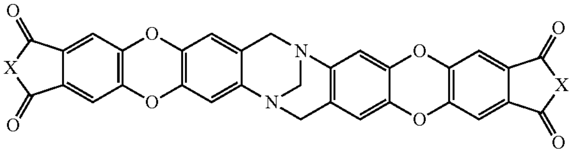

v (TBDA)

where X is O or N—$R_1$, wherein $R_1$ is a comonomer selected from the group comprising of an aryl group, a substituted aryl group, a heteroaryl group, a Tröger's base compound, or a substituted Tröger's base compound.

2. A polyimide, comprising:

reacted units of the Tröger's base complex of claim 1, wherein X is N—$R_1$ and the comonomer $R_1$ is a substituted aryl group.

3. The polyimide of claim 2, wherein the substituted aryl group is a 2,3,5,6-tetramethyl-p-phenylenediamine (TMPD).

4. A membrane film comprising the polyimide of claim 3.

5. A polyimide, comprising:

reacted units of the Tröger's base complex of claim 1, wherein X is N—$R_1$ and the comonomer $R_1$ is a substituted Tröger's base compound.

6. The polyimide of claim 5, wherein the substituted Tröger's base compound is a 1,7-diamino-6H,12H-5,11-methanodibenzo[1,5]diazocine-2,8-diol (HTB).

7. A film membrane comprising the polyimide of claim 6.

8. The polyimide of claim 2, made by a process comprising:

heating the TB complex of Formula I with a phenol to a first temperature to form a reaction mixture, wherein X is O;

adding the comonomer to the reaction mixture;

heating the reaction mixture to a second temperature;

precipitating the reaction mixture in a first organic solvent to form a solid;

precipitating the solid in a second organic solvent to form the polyimide; and drying the polyimide.

9. The membrane of claim 4, wherein the membrane film has a decomposition temperature of 410° C. to 440° C. by TGA.

10. The membrane of claim 4, wherein the gas permeability of the membrane film is in the following order: carbon dioxide>hydrogen>oxygen>methane>nitrogen.

11. The membrane of claim 7, wherein the gas permeability of the membrane film is in the following order: hydrogen>carbondioxide>oxygen>nitrogen>methane.

12. The membrane of claim 7, wherein the membrane film comprises hydrogen bonds.

13. The membrane of claim 4, wherein the membrane film has a $CO_2$ permeability of 1400 barrer to 1500 barrer.

14. The membrane of claim 7, wherein the membrane film has a $CO_2$ permeability of 60 barrer to 80 barrer.

15. The membrane of claim 4, wherein the membrane film has a $CO_2/CH_4$ selectivity of 15 to 25.

16. The membrane of claim 7, wherein the membrane film has a $CO_2/CH_4$ selectivity of 30 to 60.

17. The membrane of claim 4, wherein the membrane film has a diffusion coefficient of $CO_2$ of $2.0\times10^{-7}$ $cm^2$ $s^{-1}$ to $5.0\times10^{-7}$ $cm^2$ $s^{-1}$.

18. The membrane of claim 7, wherein the membrane film has a diffusion coefficient of $CO_2$ of $2.0\times10^{-8}$ $cm^2$ $s^{-1}$ to $3.0\times10^{-8}$ $cm^2$ $s^{-1}$.

19. The membrane of claim 4, wherein, after aging for 80 days to 100 days, the membrane film has a higher $H_2/N_2$, $H_2/CH_4$, $O_2/N_2$, and $CO_2/CH_4$ selectivity compared to the membrane film before the aging.

20. The membrane of claim 7, wherein, after aging for 40 days to 60 days, the membrane film has a higher $H_2/N_2$, $H_2/CH_4$, $O_2/N_2$, and $CO_2/CH_4$ selectivity compared to the membrane film before the aging.

* * * * *